(12) United States Patent
Moroiwa et al.

(10) Patent No.: US 8,828,636 B2
(45) Date of Patent: Sep. 9, 2014

(54) ALCOHOL COMPOUND, A POLYESTER RESIN, AN UNSATURATED PARTICLE RESIN, A RESIN PARTICLE AND AN ELECTROPHOTOGRAPHIC TONER

(75) Inventors: Tetsuji Moroiwa, Hiratsuka (JP); Nobutaka Yoshida, Hiratsuka (JP); Hiroshi Aihara, Hiratsuka (JP); Akira Yamane, Hiratsuka (JP); Kei Yamasaki, Hiratsuka (JP); Keiko Taniuchi, Hiratsuka (JP)

(73) Assignee: Japan U-Pica Company, Ltd., Tokyo (JP)

( * ) Notice: Subject to any disclaimer, the term of this patent is extended or adjusted under 35 U.S.C. 154(b) by 2 days.

(21) Appl. No.: 13/700,422

(22) PCT Filed: Mar. 2, 2011

(86) PCT No.: PCT/JP2011/001219
§ 371 (c)(1),
(2), (4) Date: Nov. 27, 2012

(87) PCT Pub. No.: WO2011/148545
PCT Pub. Date: Dec. 1, 2011

(65) Prior Publication Data
US 2013/0071785 A1 Mar. 21, 2013

(30) Foreign Application Priority Data

May 28, 2010 (JP) ................. 2010-123163
May 28, 2010 (JP) ................. 2010-123250
Feb. 18, 2011 (JP) ................. 2011-033981

(51) Int. Cl.
*G03G 9/087* (2006.01)
*C08G 65/40* (2006.01)
(Continued)

(52) U.S. Cl.
CPC .............. *C07C 69/753* (2013.01); *C08G 65/40* (2013.01); *G03G 9/08764* (2013.01); *C08G 63/199* (2013.01); *C08L 67/025* (2013.01); *G03G 9/08755* (2013.01); *C08G 65/48* (2013.01); *C09D 175/16* (2013.01); *C08G 2150/20* (2013.01); *G03G 9/08797* (2013.01); *C08G 18/8074* (2013.01); *C09D 167/025* (2013.01); *C08G 63/672* (2013.01); *C08G 63/553* (2013.01); *G03G 9/08795* (2013.01); *C09D 167/06* (2013.01); *G03G 9/0812* (2013.01); *C08G 18/672* (2013.01); *C08G 63/193* (2013.01); *C08L 67/06* (2013.01); *G03G 9/08759* (2013.01)
USPC ............. 430/109.4; 430/109.2; 524/604; 524/605; 525/440.08; 528/190; 560/190

(58) Field of Classification Search
USPC ............. 430/109.2, 109.4; 524/604, 605; 525/440.08; 528/190; 560/190
See application file for complete search history.

(56) References Cited

FOREIGN PATENT DOCUMENTS
JP 4-303849 A 10/1992
JP 5-263059 A 10/1993
(Continued)

OTHER PUBLICATIONS

Translation of JP 2007-240831 published Sep. 2007.*
(Continued)

*Primary Examiner* — Peter Vajda
(74) *Attorney, Agent, or Firm* — Birch, Stewart, Kolasch & Birch, LLP

(57) ABSTRACT

It is an object of the present invention to provide a new alcohol compound, a polyester resin, an unsaturated polyester resin, a resin particle and an electrophotographic toner using the compound capable of using the renewable resources as a part of a raw material.
An alcohol compound according to the present invention is characterized by representing the chemical formula [Chemical 1]. Furthermore, the polyester resin or the unsaturated polyester resin according to the present invention, is characterized in that the compound (wherein X is an aliphatic or an aromatic residue, Y is a refined rosin residue, a disproportionated rosin residue or a hydrogenated rosin residue, and n=0 to 1 in the formula.) is an essential component of an alcohol component. Further, the resin particle of the present invention is characterized by comprising the polyester resin.

24 Claims, 3 Drawing Sheets

(51) Int. Cl.
*C08G 63/199* (2006.01)
*C07C 69/753* (2006.01)
*C08L 67/02* (2006.01)
*C08G 65/48* (2006.01)
*C09D 175/16* (2006.01)
*C08G 18/80* (2006.01)
*C09D 167/02* (2006.01)
*C08G 63/672* (2006.01)
*C08G 63/553* (2006.01)
*C09D 167/06* (2006.01)
*G03G 9/08* (2006.01)
*C08G 18/67* (2006.01)
*C08G 63/193* (2006.01)
*C08L 67/06* (2006.01)

(56) References Cited

FOREIGN PATENT DOCUMENTS

| | | |
|---|---|---|
| JP | 6-87946 A | 3/1994 |
| JP | 2004-204033 A | 7/2004 |
| JP | 2004-263142 A | 9/2004 |
| JP | 2007-240831 * | 9/2007 |
| JP | 2007-240831 A | 9/2007 |
| JP | 2007-248704 A | 9/2007 |
| JP | 2008-262179 A | 10/2008 |

OTHER PUBLICATIONS

Takiyama Eiichiro et al., plastic material course 10, polyester resin, p. 25, Nikkan Kogyo Shimbun, Ltd. (1970).

* cited by examiner

ALCOHOL COMPOUND, A POLYESTER RESIN, AN UNSATURATED PARTICLE RESIN, A RESIN PARTICLE AND AN ELECTROPHOTOGRAPHIC TONER

This application is the National Stage under 35 U.S.C. §371 of International Application No. PCT/JP2011/001219 filed on Mar. 2, 2011, which claims priority under 35 U.S.C. §119(a)-(d) of Application No. 2010-123163 filed in Japan on May 28, 2010, Application No. 2010-123250 filed in Japan on May 28, 2010, and Application No. 2011-033981 filed in Japan on Feb. 18, 2011.

TECHNICAL FIELD

The present invention relates to a new alcohol compound, and a polyester resin, an unsaturated polyester resin, a resin particle and an electrophotographic toner by using the alcohol compound.

BACKGROUND ART

An unsaturated polyester resin is used for various purposes, such as a transportation, an electricity, a construction, a civil engineering, a residential building equipment, as a binder resin for a fiber-reinforced molded article reinforced by a glass fiber, a carbon fiber and an organic fiber etc. However, there is a still remaining problem of the warping or water resistance when molding. On the other hand, it is difficult to recycle it because it is a thermosetting resin, there is a problem as to how to treat the mill ends be generated in the molded article after used or at the time of molding. Recently, although a technique for recycling waste molded article by resolving it to monomer is developed, it is still generally treated by a landfull or an incineration. Therefore, there is a problem that carbon dioxide generated by the degradation caused by the microorganism or at the time of the incineration makes it possible to accelerate the global warming by a greenhouse gas.

Although a polyester resin is used in various fields as a composition or a material for modification, for a powder coating, an electrophotographic developer, an adhesive, an ultraviolet cure ink etc., in an environment strictly required for a water resistance or a moisture resistance, there are large number of cases which can not be applicable because there is a case that a blister occurs on a coating film, or there is a case that it is impossible to exercise a primary performance since the hydrolysis of the molecular chain comes about.

The polyester resin is used in various fields for a fiber, a packaging material, fiber-reinforced plastic, a coating material, a adhesive or an electrophotographic developer other then the above mentioned powder coating, electrophotographic developer, adhesive or ultraviolet cure ink, the amount used for their becomes enormous amount. Therefore, the amount of a raw material derived from a fossil fuel as used for these polyester resin, or the amount of carbon dioxide be generated at the time of the incineration treatment of the polyester resin after used, have get to a level which can not ignore.

In recent years, a plastic derived from a raw material obtained by the renewable biomass resources has been actively developed. One of the meaning of the plastic derived from these biomass resources is because a plant absorbs repeatedly the carbon dioxide generated at the time of treating these plastic by the landfill, or at the time of treating them by the incineration, and the biomass resources are recycled so that the amount of carbon dioxide on environment could have substantively little influence, so called carbon-neutral could be put into practice.

However, at present, a polylactic acid based material most actively developed has limited uses because it's water resistance, moisture resistance, chemical resistance and mechanical properties are less than that of the conventional polyester.

As the unsaturated polyester, for example, it is known that the unsaturated polyester used for adduct of rosin and maleic anhydride as a saturated acid (Nonpatent literature 1).

As the saturated polyester, it is known that the saturated polyester used for adduct of rosin and maleic anhydride as a saturated acid (Nonpatent literature 1), there is a description that the above polyester resin has an excellent alkali resistance and acid resistance. Furthermore, as an example, it is known that a reaction product of a long-chain epoxy resin and rosin, three or more—functional epoxy resin and rosin is used as an material of the composition (Patent Literatures 1 and 2).

In the field of an electrophotographic toner which is one of the application of the polyester resin, recently, a toner having a reduced diameter and a narrow particle size distribution is required because of the increasing demand for the high-quality image. A method of producing a toner using a phase inversion phenomenon is known as a method of producing a toner having a reduced diameter and a uniform particle size (Patent Literature 3). This method is carried out by causing the phase inversion by adding an aqueous dispersion liquid to a resin solution made by dissolving a resin into a non-water soluble organic solvent, and thereby emulsifying to form an O/W emulsion, and thereby removing the organic solvent by applying heat to the O/W emulsion with stirring to separate out a resin particle. According to the phase inversion, a process can be simplified to obtain a resin particle having a uniform particle size by using a relatively simple method, and it is possible to improve production efficiency as well as to attain the reduction of cost. Furthermore, it is possible to use a various sort of a resin, and to broaden the application of the obtained resin particle, comparing with a pulverizing method or a suspension polymerization method etc.

Moreover, a method of producing a toner having a reduced diameter using a polylactic acid based resin as a raw material, according to a method of the phase inversion is known (Patent Literature 4).

Further, a method of producing water dispersion using polyester containing carboxyl groups as a raw material, according to a method of the phase inversion is known (Patent Literature 5).

PRIOR ART LITERATURE

Patent Literature

Patent literature 1: JP-A-2007-240831
Patent literature 2: JP-A-2007-240704
Patent literature 3: JP-A-H4-303849
Patent literature 4: JP-A-2008-262179
Patent literature 5: JP-A-2004-204033

Nonpatent Literature

Nonpatent literature 1: Eiichiro Takiyama et al., plastic material course 10, polyester resin, page 25, Nikkan Kogyo Shimbun, Ltd. (1970)

DISCLOSURE OF THE INVENTION

Problems to be Resolved by the Invention

However, in the past, although in the unsaturated polyester resin there is an example that an aliphatic dicarboxylic acid and an aliphatic monocarboxylic acid derived from fats and oils are used as a raw material derived from the biomass resources, it is main object to modify a performance as usage, there are no suggestions concerning the positive use of a raw material derived from the biomass resources from the viewpoint of the environmental load.

Therefore, the development of the unsaturated polyester resin using a raw material derived from the biomass material makes it possible to reduce the environmental load, and having the same performance or more than that of an unsaturated polyester resin derived from a raw material from the fossil fuel, has been desired.

Furthermore, in the polyester resin, in the above patent literatures 1 and 2, both literatures are premised on the use by mixing the product of a reaction of rosin and epoxy resin, and other polyester, and the content of rosin in the mixed resin composition decreases, and it is inadequate to express the water resistance or the moisture resistance of rosin compound. Moreover, in the case of the use of the polyfunctional epoxy resin, it may not obtain an intended polyester because the generated compound becomes a polyfunctional alcohol, and the polyester is branched or crosslinked (consequent gelling).

Therefore, the development of the polyester resin makes it possible to reduce the environmental load, and having the same performance or more than that of a polyester resin using a raw material derived from the fossil fuel in a water resistance, a moisture resistance, a coefficient of shrinkage and a mechanical property, has been desired.

In this surroundings, although it is known as a common knowledge that the use of a rosin based compound as a raw material of the unsaturated polyester resin renders the improvement of a water resistance and a moisture resistance, there are still problems that it is impossible to exercise a desired performance because it is impossible to obtain a resin having a long molecular chain and an excellent mechanical property since the rosin based compound is monofunctional material, and it is impossible to react only the end of a molecular chain to make reduced it's content ever if one try to obtain a resin having a long molecular chain.

Moreover, in a resin particle and an electrophotographic toner, there is a following problem. Namely, in the above patent literature 4, there is a problem that solubility for the organic solvent is extremely low because of a high crystallinity of a polylactic acid polymerized by D type or L type of the same monomer component. Further, in the above patent literature 5, in the present, an extremely excess neutralizing agent for a carboxyl group in a polyester resin is required in order to obtain a water dispersion having a narrow particle size distribution, and a cleaning of the extremely excess neutralizing agent gives a large number of the treatment of the wastewater etc., and thereby increasing an environmental load.

Therefore, it is an object of the present invention as to the unsaturated polyester resin to provide a polyester resin having an excellent performance in a water resistance, a low shrinkage and a mechanical property, and making it possible to reduce the effects on the environmental load in a various sort of the field.

Moreover, it is an object of the present invention as to the saturated polyester resin to provide a polyester resin having an excellent performance in a water resistance, a moisture resistance and a mechanical property, and making it possible to reduce the environmental load in a various sort of the field.

Furthermore, it is an object of the present invention as to a resin particle etc., to provide a resin particle and an electrophotographic toner capable of using the renewable material as a part of a raw material.

Means of Solving the Problems

In order to accomplish the above objects, the present inventors made strenuous studies. As a result, the inventors discovered new compound and the unsaturated polyester resin, achieved the present invention.

That is, a compound according to the present invention is characterized by representing the following chemical formula [Chemical 1]:

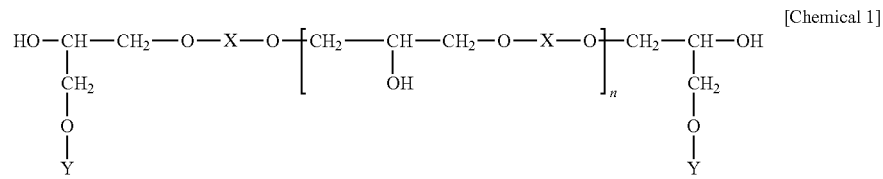

[Chemical 1]

(wherein X is an aliphatic or an aromatic residue, Y is a refined rosin residue, a disproportionated rosin residue or a hydrogenated rosin residue, and n=0 to 1 in the formula.).

Furthermore, in a preferred embodiment of above mentioned compound according to the present invention, the compound is characterized by being obtained by the addition reaction of one or more selected from the group consisting of a refined rosin, a disproportionated rosin, and a hydrogenated rosin, to an epoxy group of a compound having two epoxy group in one molecule and shown in the following chemical formula [Chemical 2]:

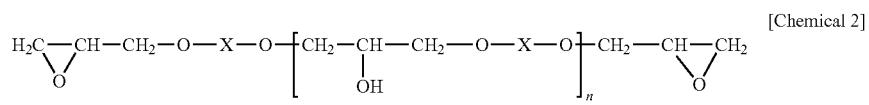

[Chemical 2]

(wherein X is an aliphatic or an aromatic residue, and n=0 to 1 in the formula.).

Furthermore, an unsaturated polyester resin according to the present invention is characterized in that the compound according to the present invention is an essential component of an alcohol component.

Furthermore, in a preferred embodiment of the unsaturated polyester resin according to the present invention, the invention is characterized in that the compound according to the present invention is contained at 20 percent by weigh or more as a raw material of unsaturated polyester.

Furthermore, a premix molding compound according to the present invention is characterized in that above mentioned unsaturated polyester resin according to the present invention is contained.

Furthermore, in a preferred embodiment of the premix molding compound according to the present invention, the invention is characterized in that the premix molding compound is a sheet molding compound, or a bulk molding compound.

Further, in order to accomplish the above objects, the present inventors made strenuous studies. As a result, the inventors discovered new alcohol compound and the polyester resin, achieved the present invention.

That is, the polyester resin according to the present invention is characterized in that a compound shown in the following chemical formula [Chemical 3], is an essential component of an alcohol component:

acterized in that the compound shown in the above [Chemical 3] is contained at 20 percent by weigh or more as a raw material of polyester.

Furthermore, a resin composition for the powder coating according to the present invention is characterized in that the polyester resin according to the present invention is used.

Furthermore, a resin composition for an electrophotographic developer according to the present invention is characterized in that the polyester resin according to the present invention is used.

Furthermore, an urethane acrylate resin according to the present invention is characterized in that the polyester resin according to the present invention is contained and modified by isocyanate.

Further, in order to accomplish the above objects, the present inventors made strenuous studies. As a result, the inventors discovered new resin particle, achieved the present invention. That is, the summary of the invention is as follows.

That is, a resin particle according to the present invention is characterized in that a compound shown in the following chemical formula [chemical 5], is an essential component of an alcohol component:

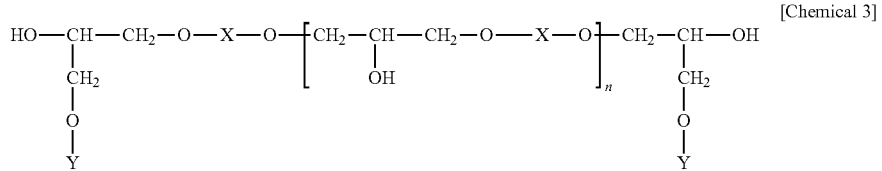

[Chemical 3]

(wherein X is an aliphatic or an aromatic residue, Y is a refined rosin residue, a disproportionated rosin residue or a hydrogenated rosin residue, and n=0 to 1 in the formula.).

Furthermore, in a preferred embodiment of the polyester resin according to the present invention, the invention is characterized in that the compound (which is shown in the above formula [Chemical 3]) is obtained by the addition reaction of at least one component selected from the group consisting of a refined rosin, a disproportionated rosin, and a hydrogenated rosin, to an epoxy group of a compound having two epoxy group in one molecule and shown in the following chemical formula [Chemical 4]:

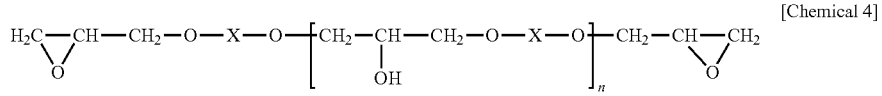

[Chemical 4]

(wherein X is an aliphatic or an aromatic residue, and n=0 to 1 in the formula.).

Furthermore, in a preferred embodiment of the polyester resin according to the present invention, the invention is char-

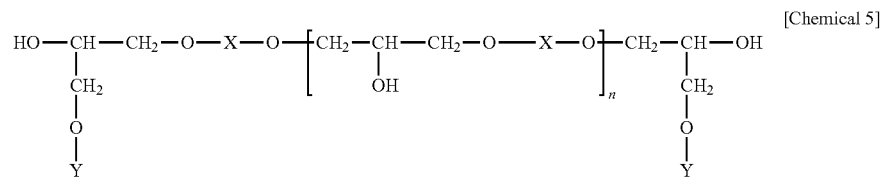

[Chemical 5]

(wherein X is an aliphatic or an aromatic residue, Y is a refined rosin residue, a disproportionated rosin residue or a hydrogenated rosin residue, and n=0 to 1 in the formula.).

Furthermore, in a preferred embodiment of the resin particle according to the present invention, the invention is characterized in that a volume average particle size of the resin particle is within a range from 0.01 to 1 μm.

Furthermore, in a preferred embodiment of the resin particle according to the present invention, the invention is characterized in that the resin particle is obtained by causing the phase inversion by means of adding a neutralizing agent and a water-based medium into a resin solution made by dissolving the polyester resin into an organic solvent, and thereby forming an O/W emulsion of a resin particle, and further removing the organic solvent from an O/W emulsion of a resin particle.

Furthermore, in a preferred embodiment of the resin particle according to the present invention, the invention is characterized in that the compound is obtained by the addition reaction of at least one component selected from the group consisting of a refined rosin, a disproportionated rosin, and a hydrogenated rosin, to an epoxy group of a compound having two epoxy group in one molecule and shown in the following chemical formula [Chemical 6]:

(wherein X is an aliphatic or an aromatic residue, Y is a refined rosin residue, a disproportionated rosin residue or a hydrogenated rosin residue, and n=0 to 1 in the formula.).

Furthermore, in a preferred embodiment of the electrophotographic toner according to the present invention, the invention is characterized in that an average particle diameter of the resin particle is within a range from 0.01 to 1 μm.

Furthermore, in a preferred embodiment of the electrophotographic toner according to the present invention, the invention is characterized in that the toner comprises a resin particle obtained by causing the phase inversion by means of adding a neutralizing agent and a water-based medium into a resin solution made by dissolving the polyester resin into an organic solvent, and thereby forming an O/W emulsion of a resin particle, and further removing the organic solvent from an O/W emulsion of a resin particle.

Furthermore, in a preferred embodiment of the electrophotographic toner according to the present invention, the invention is characterized in that the compound is obtained by the addition reaction of at least one component selected from the group consisting of a refined rosin, a disproportionated rosin, and a hydrogenated rosin, to an epoxy group of a compound having two epoxy group in one molecule and shown in the following chemical formula [Chemical 8]:

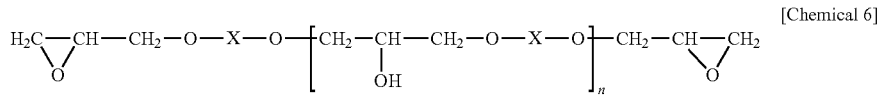

[Chemical 6]

(wherein X is an aliphatic or an aromatic residue, and n=0 to 1 in the formula.).

Furthermore, in a preferred embodiment of the resin particle according to the present invention, the invention is characterized in that the compound shown in the above [Chemical 5] is contained at 20 percent by weigh or more as a raw material of polyester.

Furthermore, in a preferred embodiment of the resin particle according to the present invention, the invention is characterized in that the neutralizing agent is contained at 0.8 to 1.7 equivalent weight per equivalent of a carboxyl group.

Furthermore, an electrophotographic toner according to the present invention is characterized in that the electrophotographic toner comprises at least polyester resin and colorant, and comprises a resin particle comprising the polyester resin wherein a compound shown in the following chemical formula [Chemical 7], is an essential component of an alcohol component:

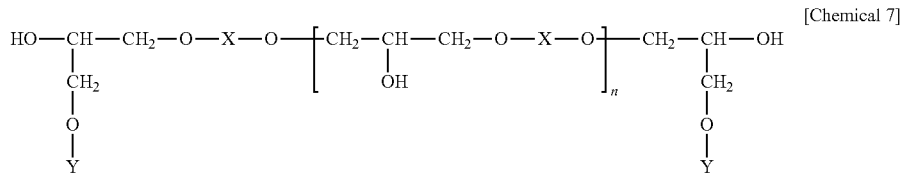

[Chemical 7]

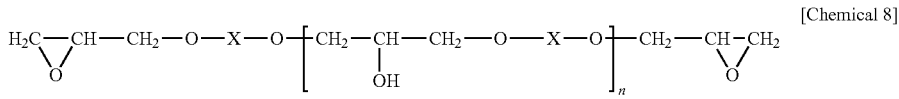

[Chemical 8]

(wherein X is an aliphatic or an aromatic residue, and n=0 to 1 in the formula.).

Furthermore, in a preferred embodiment of the electrophotographic toner according to the present invention, the invention is characterized in that the compound shown in the above [chemical 7] is contained at 20 percent by weigh or more as a raw material of polyester.

Furthermore, in a preferred embodiment of the electrophotographic toner according to the present invention, the invention is characterized in that the neutralizing agent is contained at 0.8 to 1.7 equivalent per equivalent of a carboxyl group.

Effect of Invention

The unsaturated polyester resin according to the present invention has an advantage effect that it has an excellent performance in a water resistance, a low shrinkage and a mechanical property even if it is compared with that of the unsaturated polyester resin using a raw material derived from a fossil fuel.

The unsaturated polyester resin according to the present invention has an advantage effect that since it has a low water absorption, and has a high strength of a resin, and has a low shrinkage at the time of curing, compared with the prior art, a fiber-reinforced plastic (hereinafter called FRP) using the resin has an excellent water resistance and is manufactured with high dimensional accuracy. Moreover, it has an advantage effect that it is possible to obtain a molded article making it possible to reduce the environmental load since it uses a raw material derived from the biomass material.

Furthermore, a sheet molding compound and a bulk molding compound containing the unsaturated polyester resin according to the present invention has an advantage effect that it is possible to obtain a molded article having an excellent water resistance and being manufactured with high dimensional accuracy in the same way as mentioned above. That is, it makes it possible to expand a range of an application of a FRP.

Furthermore, the polyester resin according to the present invention has an advantage effect that it has a low water absorption, and has a high strength of a resin comparing with the polyester resin according to the prior art, and further it is possible to reduce the environmental load since it uses a raw material derived from the biomass material.

A powder coating containing the polyester resin according to the present invention has an advantage effect that it is possible to use it under the various sort of the environment. In the same way, an electrographic developer containing the polyester resin according to the present invention has an advantage effect that it is possible to obtain a desired developer as planed since it does not tend to take place a hydrolysis when kneading or emulsifying. Furthermore, a polyester urethane acrylate containing the polyester resin as a raw material according to the present invention has an advantage effect that it is possible to form a coated film having a good adhesiveness and an excellent water resistance and a lower shrinkage, by means of a thermosetting and an ultraviolet curing. In this matter, it is possible to apply it in a various sort of field.

Furthermore, according to a resin particle of the present invention, it has an advantage effect that it is possible to provide a resin particle having a narrow particle size distribution, and a toner having a small particle size and a narrow particle size distribution capable of responding a demand of a high-quality image. Furthermore, according to an electrophotographic toner of the present invention, it has an advantage effect that in addition to the environmental characteristics that a wastewater during a manufacturing process is small etc., it is possible to produce a resin particle and a toner having a narrow particle size distribution.

MODE FOR CARRYING OUT THE INVENTION

Figure 1:
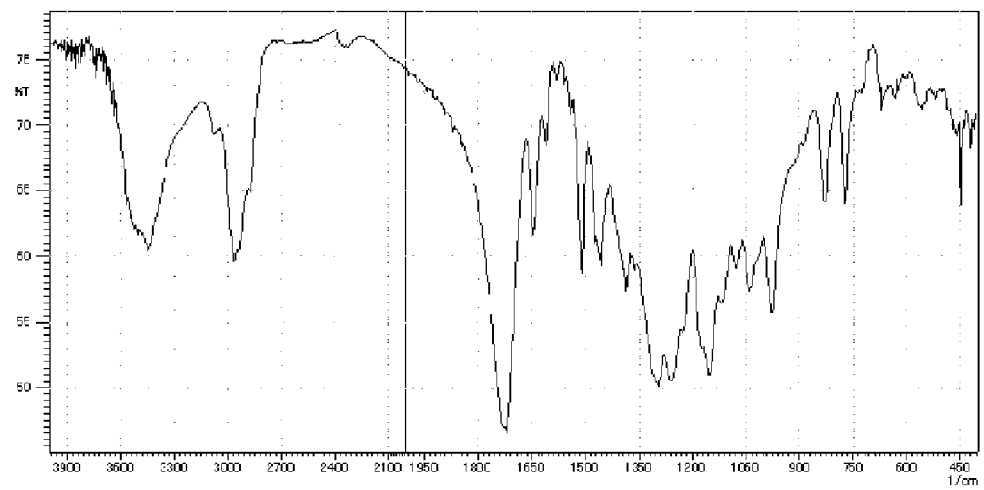
FIG. 1 gives an IR (an infrared absorption spectrum) chart of the unsaturated polyester resin obtained by an example of the composition 1.
Figure 2:
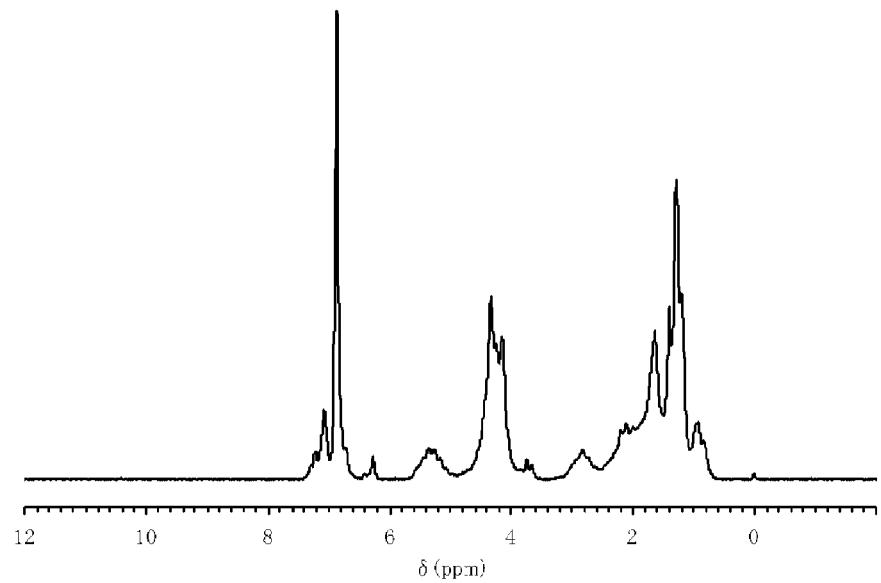
FIG. 2 gives a $^1$H-NMR (nuclear magnetic resonance) spectrum of the unsaturated polyester resin obtained by an example of the composition 1.
Figure 3:
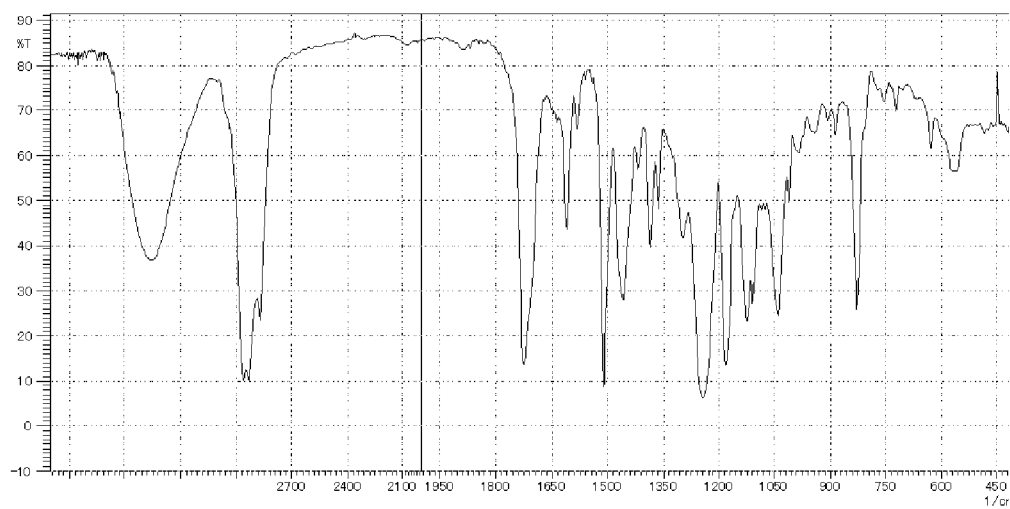
FIG. 3 gives an IR (an infrared absorption spectrum) chart of the alcohol compound obtained by an example of the composition 1.
Figure 4:
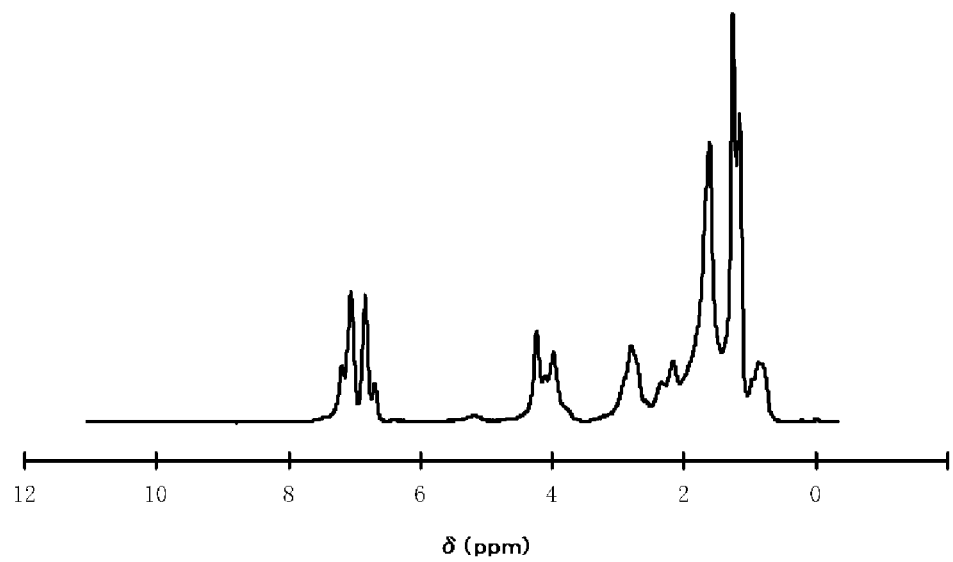
FIG. 4 gives a $^1$H-NMR (nuclear magnetic resonance) spectrum of the alcohol compound obtained by an example of the composition 1.
Figure 5:
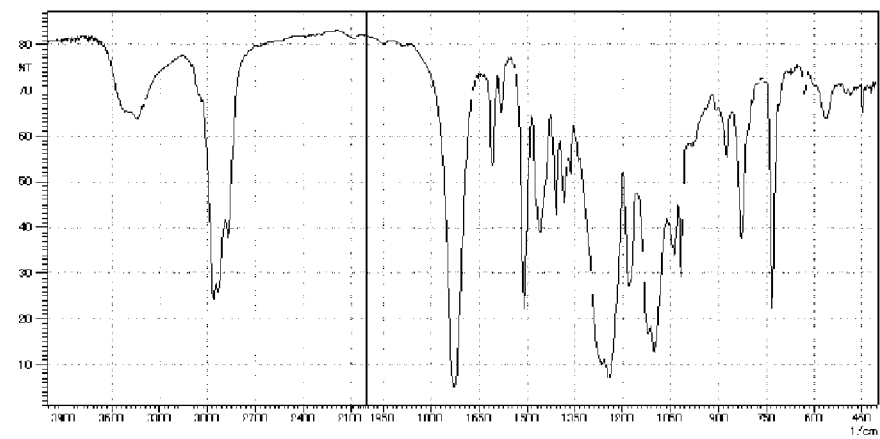
FIG. 5 gives an IR (an infrared absorption spectrum) chart of the polyester resin obtained by an example of the composition 6.
Figure 6:
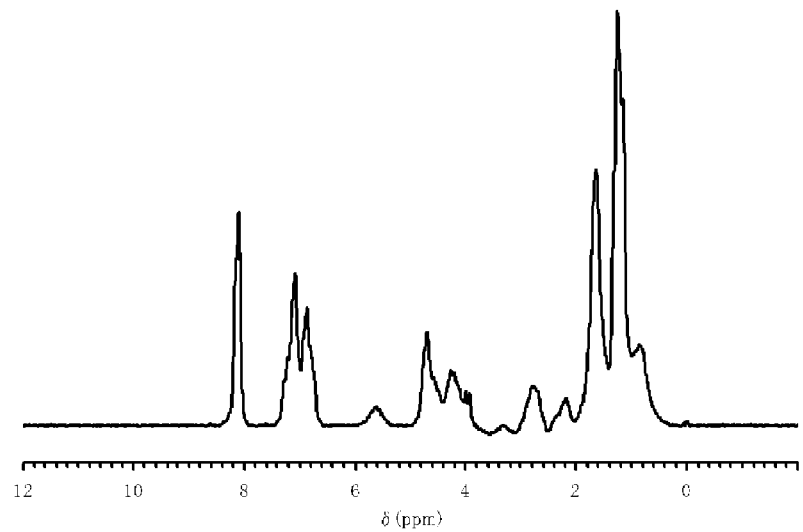
FIG. 6 gives a $^1$H-NMR (nuclear magnetic resonance) spectrum of the polyester resin obtained by an example of the composition 6.

First of all, the detailed explanations of the new alcohol compound according to the present invention are described below.

A compound according to the present invention is a compound characterized by representing the following chemical formula [Chemical 9]:

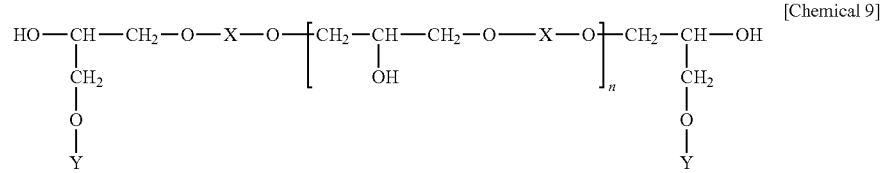

[Chemical 9]

(wherein X is an aliphatic or an aromatic residue, Y is a refined rosin residue, a disproportionated rosin residue or a hydrogenated rosin residue, and n=0 to 1 in the formula.).

Furthermore, in a preferred embodiment of the compound according to the present invention, the compound shown in the above [chemical 9] is obtained by the addition reaction of at least one component selected from the group consisting of a refined rosin, a disproportionated rosin, and a hydrogenated rosin, to an epoxy group of a compound having two epoxy group in one molecule and shown in the following chemical formula [Chemical 10]:

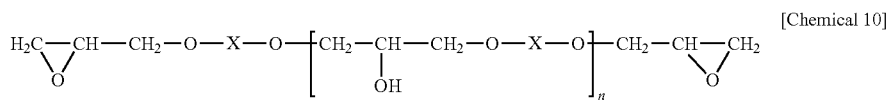

[Chemical 10]

(wherein X is an aliphatic or an aromatic residue, and n=0 to 1 in the formula.).

At this moment, in the present specification, a rosin means that it is a natural resin obtained from pines and the main component of the natural resin is resin acid such as abietic acid, palustric acid, neoabietic acid, pimaric acid, dehydroabietic acid, isopimaric acid, sandaracopimaric acid, dihydroabietic acid and mixture thereof. A rosin can be classified broadly into a tall rosin obtained by a tall oil obtained as a by-product during a process of manufacturing a pulp, a gum rosin obtained by a raw pine resin, a wood rosin obtained by a stump of a pine etc., a rosin used for the present invention is at least one component selected from the group consisting of a refined rosin, a disproportionated rosin, and a hydrogenated rosin.

Furthermore, an unsaturated polyester resin, a saturated polyester resin, a resin particle and an electrophotographic toner according to the present invention, is characterized in that the compound according to the above present invention is an essential component of an alcohol component.

Furthermore, a manufacturing process wherein an unsaturated polyester resin, a saturated polyester resin, a resin particle and an electrophotographic toner according to the present invention, is characterized in that it applies a two-stage reaction process, and in a first-stage reaction the below compound (a) is obtained, followed by produced by the same manner as the conventional process in a second-stage.

At first, a compound (a) ([Chemical 12]) will be explained which is shown in the below chemical formula (2) and becomes a raw material of an essential alcohol component of the unsaturated polyester resin according to the present invention. The compound (a), for example, can be obtained by the addition reaction at least one component selected from the group consisting of a refined rosin, a disproportionated rosin, and a hydrogenated rosin, to an epoxy group of a compound having two epoxy group in one molecule and shown in the following chemical formula (1) ([Chemical 11]), under the condition of the existence of a known catalyst, under nitrogen, at a temperature of 130° C. to 185° C., until less than 5 mg KOH/g of the acid value.

Chemical formula (1) [Chemical 11])

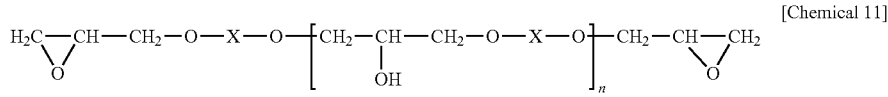

[Chemical 11]

(wherein X is an aliphatic or an aromatic residue, and n=0 to 1 in the formula.).

Chemical formula (2) [Chemical 12])

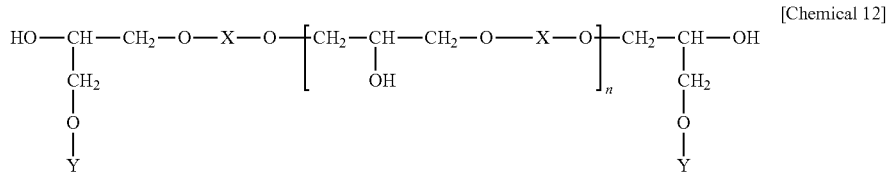

[Chemical 12]

(wherein X is an aliphatic or an aromatic residue, Y is a refined rosin residue, a disproportionated rosin residue or a hydrogenated rosin residue, and n=0 to 1 in the formula.).

The reaction temperature is not particularly limited, but a reaction temperature of the first stage is preferably less than 185° C., from a viewpoint that in the case that a reaction temperature of the first stage is 185° C. or more, a condensation reaction of an unreacted rosin with a hydroxyl group existing in the molecule of the epoxy compound, or a hydroxyl group produced by the reaction with a rosin, and therefore, it may not obtain a desired alcohol for a raw material of the polyester.

Furthermore, from a viewpoint of the reduction of the reaction time, preferably it is possible to react it at 130° C. or more. Although the reaction end point of the first stage is defined by the acid value, there are possibilities that an unsaturated polyester having a desired molecular weight may not be obtained because a reacted rosin can preventing a formulation of the molecular chain if a reaction makes the shift to the second stage under the condition that the acid value is 5 mgKOH/g or more. Furthermore, there are possibilities that a desired unsaturated polyester may not be obtained because a produced compound becomes a polyfunctional alcohol, and a viscosity tend to be high because of the branching of the unsaturated polyester, or gelling occurs if the number of cycles n of the compound having two epoxy group in one molecule and shown in the chemical formula (1) is 1 or more. The additive amount of the compound (a) produced by the first stage is not particularly limited. The compound (a) produced at first stage of reaction is preferably contained at 20 percent by weigh or more as a raw material of a desired unsaturated polyester, from a viewpoint that an effect on a water resistance or a mechanical property is low, and an effect for reducing the environment load is low too.

Although the compound having two epoxy group in one molecule and shown in the chemical formula (1) ([Chemical 11]) is not particularly limited, however, it can be manufactured by combining phenols having two phenolic hydroxyl group in one molecule and alcohols having two hydroxyl group in one molecule to be epoxidized with epichlorohydrin according to a known method. Furthermore, it is possible to use a commercially available epoxy compound too. As the commercially available epoxy compound, for example, mention may be made of a bisphenol A type of an epoxy compound such as "JER828" made by Mitsubishi Chemical Corporation, "AER260" made by Asahi Kasei Chemicals Corporation, "EPICLON840, 850" made by DIC Corporation, "Epotohto 128" made by Tohto Kasei Co., Ltd., "D. E. R. 317" and "D. E. R. 331" made by Dow Chemical Company, "SUMIEPDXY ESA-011" made by Sumitomo Chemical Co., Ltd., a bisphenol F type of an epoxy compound such as "EPICLON830S" made by DIC Corporation, "EPIKOTE807" made by Mitsubishi Chemical Corporation, "Epotohto YDF-170" made by Tohto Kasei Co., Ltd., "AralditeXPY306" made by Asahi Kasei Chemicals Corporation, a bisphenol S type of an epoxy compound such as "EBPS-200" made by Nippon Kayaku Co., Ltd., "EPX-30" made by Asahi Denka Kogyo K.K., "EPICLON EXA1514" made by DIC Corporation, a bisphenol fluorene type of an epoxy compound such as "BPFG" made by Osaka Gas Chemicals Co., Ltd., a bixylenol type or a biphenyl type of the epoxy compound such as "YL-6056" and "YX-4000" or the mixture thereof made by Mitsubishi Chemical Corporation, a hydrogenated bisphenol A type of an epoxy compound such as "HBE-100" made by New Japan Chemical Co., Ltd., "Epo-tohto ST-2004" made by Tohto Kasei Co., Ltd., a brominated bisphenol A type of an epoxy compound such as "EPICLON152" made by DIC Corporation, "SR-BSP" made by Sakamoto Yakuhin Kogyo Co., Ltd., "Epotohto YDB-400" made by Tohto Kasei Co., Ltd., "D. E. R. 542" made by Dow Chemical Company, "AER8018" made by Asahi Kasei Chemicals Corporation, "SUMIEPDXY ESB-400" made by Sumitomo Chemical Co., Ltd., an epoxy compound having a naphthalene skeleton such as a name of article "ESN-190" made by Nippon Steel Chemical Co., Ltd., a name of article "HP-4032" made by DIC Corporation, an aliphatic epoxy compound such as a name of article "EPOLIGHT 400E", "EPOLIGHT 400P" and "EPOLIGHT 1600" made by kyoeisha Chemical Co., Ltd., "SR-NPG" and "SR-16HL" made by Sakamoto Yakuhin Kogyo Co., Ltd., however it is not limited to them. It is possible to use it by itself or by the combination of two or more among the above compound.

Next, although as carboxylic acid and alcohols which are a raw material of an unsaturated polyester used for the second stage reaction, those of being manufactured thermochemically derived from a fossil fuel according to the prior art, those of being manufactured biochemically derived from a raw material of animals and plants, or those of being manufactured by the thermochemical treatment of a compound produced biochemically derived from a raw material of animals and plants, can be used, it is preferable to use those of being manufactured biochemically derived from a raw material of animals and plants, or those of being manufactured by the thermochemical treatment of a compound produced biochemically derived from a raw material of animals and plants, in the viewpoint of an environmental load and a carbon-neutral. In turn, unsaturated acid, saturated acid and alcohol will be explained.

Although as an unsaturated acid, mention may be made of maleic anhydride, maleic acid, and fumaric acid produced thermochemically derived from a fossil fuel in the known art, it is preferable to be maleic anhydride, maleic acid, and fumaric acid derived from succinic acid of the biomass from a viewpoint of an environmental load and a carbon-neutral.

As a saturated acid, mention may be made of the acids produced thermochemically derived from a fossil fuel in the known art, such as phthalic acid, terephthalic acid, isophthalic acid, biphenyldicarboxylic acid, naphthalenedicarboxylic acid, 5-tert-butyl-1,3-benzenedicarboxylic acid and acid anhydride thereof, and a derivative such as a lower alkyl ester etc. It is possible to use a lower alkyl ester of terephthalic acid and isophthalic acid, as an example of a lower alkyl ester of terephthalic acid and isophthalic acid, although mention may be made of dimethyl terephthalate, dimethyl isophthalate, diethyl terephthalate, diethyl isophthalate, dibutyl terephthalate, dibutyl isophthalate, it is preferable to be dimethyl terephthalate or dimethyl isophthalate, from a viewpoint of a cost and a handling. As carboxylic acid manufactured biochemically derived from a raw material of animals and plants, or those of being manufactured by the thermochemical treatment of a compound produced biochemically derived from a raw material of animals and plants, mention may be made of dimer acid, succinic acid, itaconic acid, 2,5-furandicarboxylic acid etc. It is possible to use it by itself or by the combination of two or more among the above unsaturated acid, saturated acid or a lower alkyl ester.

Furthermore, it is possible to use a trivalent or more aromatic polycarboxylic acid too, in a range that dose not impair effects of the present invention. As a trivalent or more aromatic polycarboxylic acid, mention may be made of trimellitic acid, pyromellitic acid, naphthalenetricarboxylic acid, benzophenon tetracarboxylic acid, biphenyl tetracarboxylic acid or anhydride thereof, it is possible to use it by itself or by the combination of two or more among the above trivalent or more aromatic polycarboxylic acid. As trivalent or more aromatic polycarboxylic acid, it is preferable to be trimellitic anhydride from a viewpoint of the reactivity.

As alcohols, mention may be made of alcohols manufactured thermochemically derived from fossil fuel of prior art, such as aliphatic alcohol and etherified diphenol. As an example of aliphatic alcohol, for example, mention may be made of ethylene glycol, 1,2-propanediol, 1,3-propanediol, 1,2-butanediol, 1,3-butanediol, 1,4-butanediol, 2,3-butanediol, 1,4-butenediol, 2-methyl-1,3-propanediol, 1,5-pentanediol, neopentyl glycol, 2-ethyl-2-methylpropane-1,3-diol, 2-butyl-2-ethylpropane-1,3-diol, 1,6-hexanediol, 3-methyl-1,5-pentanediol, 2-ethyl-1,3-hexanediol, 2,4-dimethyl-1,5-pentanediol, 2,2,4-trimethyl-1,3-pentanediol, 1,7-heptanediol, 1,8-octanediol, 1,9-nonanediol, 1,10-decanediol, 3-hydroxy-2,2-dimethyl propyl-3-hydroxyl-2,2-dimethyl propanoate, diethylene glycol, triethylene glycol, dipropylene glycol etc. As aliphatic alcohol, ethylene glycol, 1,3-propanediol, neopentyl glycol is preferable from a viewpoint of the reactivity with acid and glass-transition temperature of resin. It is possible to use these aliphatic alcohol by themselves or by the combination of two or more among the above alcohol. Moreover, in the present invention, together with the aliphatic alcohol, further, it is possible to use etherified diphenol. The etherified diphenol is a diol obtained by the addition reaction of alkylene oxide with bisphenol A, as the alkylene oxide, mention may be made of ethylene oxide or propylene oxide, and it is preferable that the average number of moles added is 2 to 16 moles to 1 mole of bisphenol A. It is preferable to use ethylene glycol, 1,2-propanediol, 1,3-propanediol, 1,4-butanediol biochemically produced from the raw material of animals and plants, from a viewpoint of an environmental load and a carbon-neutral.

As other component of the raw material of polyester, it is possible to use alicyclic polycarboxylic acid such as 1,3-cyclohexanedicarboxylic acid, 1,4-cyclohexanedicarboxylic acid, cyclohexanecarboxylic acid, tetrahydrophthalic anhydride, methyltetrahydrophthalic anhydride, endo-methylene-tetrahydrophthalic anhydride, halogen-containing dicarboxylic acid such as het acid, tetrabromophthalic anhydride, hydroxycarboxylic acid such as lactic acid, 3-hydroxybutanoic acid, 3-hydroxy-4-ethoxybenzoic acid too, in a range that dose not impair objects of the present invention.

The unsaturated polyester resin according to the present invention is prepared by a known common method by using the above compound (a) ([Chemical 1]), a predetermined carboxylic acid component, and an alcohol component as a raw material. It is possible to apply any method of a transesterification reaction or a direct esterification reaction as these reaction methods. Further, it is possible to accelerate polycondensation by means of a method of increasing the reaction temperature by applying pressure, a method of reducing pressure or a method of flowing inert gas under normal pressures, too. A reaction at second stage may be conducted without a catalyst, a reaction may be accelerated by using a known common reaction catalyst such as at least one metallic compound selected from the group consisting of antimony, titanium, tin, zinc, aluminum and manganese. It is preferable that the additive amount of these reaction catalysts is within a range from 0.01 to 1.0 parts by weight for 100 parts by weight of the total amount of carboxylic acid component and alcohol component.

It is possible to prepare unsaturated polyester resin by means of mixing a predetermined amount of unsaturated polyester and a polymerizable monomer to dissolve in each other, or mixing in each other.

As a polymerizable monomer used in the present invention, for example, mention may be made of styrene, vinyl toluene, α-methylstyrene, vinyl acetate, methyl methacrylate, mathacrylic acid, acrylic acid, benzyl (meta) acrylate, n-butyl (meta) acrylate, i-butyl (meta) acrylate, t-butyl (meta) acrylate, 2-ethylhexyl (meta) acrylate, lauryl (meta) acrylate, tridecyl (meta) acrylate, stearyl (meta) acrylate, glycidyl (meta) acrylate, hydroxypropyl (meta) acrylate, 2-methoxyethyl (meta) acrylate, 2-ethoxyethyl (meta) acrylate, cyclohexyl (meta) acrylate, isobornyl (meta) acrylate, norbornyl (meta) acrylate, dicyclopentenyl (meta) acrylate, dicyclopenthanil (meta) acrylate, dicyclopentenyloxyethyl (meta) acrylate, acryl (meta) acrylate, 2-hydroxyethyl (meta) acrylate, succinic acid 2-(meta) acryloyloxyethyl, maleic acid 2-(meta) acryloyloxyethyl, phthalic acid 2-(meta) acryloyloxyethyl, hexahydro phthalic acid 2-(meta) acryoyloxyethyl, pentamethylpiperidyl (meta) acrylate, tetramethylpiperidyl (meta) acrylate, dimethylaminoethyl (meta) acrylate, diethylaminoethyl (meta) acrylate etc., which are used from the past. These two or more may be used by mixing properly.

In the present invention, for example, it is possible to dissolve 100 parts by weight of the unsaturated polyester with 20 to 120 parts by weight of the polymerizable monomer. Preferably, it is possible to dissolve 100 parts by weight of the unsaturated polyester with 40 to 100 parts by weight of the polymerizable monomer. In that case that the amount of the polymerizable monomer is less than 40 parts by weight for 100 parts by weight of the unsaturated polyester, a viscosity may become extremely high and impair moldability. In that case that the amount of the polymerizable monomer is 100 parts by weight or more for 100 parts by weight of the unsaturated polyester, a viscosity may impair a performance of the obtained curing molded article. When dissolving or mixing the unsaturated polyester with the polymerizable monomer, in order to prepare stably with no gelling, and in order to keep a pot life during molding of the prepared unsaturated polyester, and what is more, in order to provide stability for storage of the prepared unsaturated polyester, in general, it is possible to add a polymerization inhibitor. As a polymerization inhibitor, for example, mention may be made of polyhydric phenol based polymerization inhibitor such as hydroquinone, parabenzquinone, methylhydroquinone, trimethylhydroquinone. It is possible to use these polymerization inhibitors, in general, within a range from 0.001 to 0.5% by weight, preferably within a range from 0.005 to 0.15% by weight in the unsaturated polyester resin of the present invention.

In the unsaturated polyester resin of the present invention, it is possible to be cured under room temperature or application of heat by adding a radical curing agent generally used for the unsaturated polyester resin, and a curing accelerator according to need. Further, it is possible to be cured by adding a photoinitiator to irradiate visible ray, ultraviolet ray and electron ray.

As a radical curing agent, for example, it is possible to use a known agent from the past, such as ketoneperoxide series such as methyl ethyl ketoneperoxide, acetylacetone peroxide, diacylperoxide system such as benzoylperoxide, peroxyester series such as t-butylperoxybenzoate, hydroperoxide series such as cumene hydroperoxide, dialkylperoxide series such as dicumyl peroxide etc. The additive amount of the curing agent is within a range from 0.05 to 5 parts by weight for 100 parts by weight of the unsaturated polyester resin.

As a curing accelerator, it is possible to use a known accelerator in the prior art, for example, such as a metal soap class such as cobalt naphthenate, cobalt octylate, zinc octylate, vanadium octylate, copper naphthenate, barium naphthenate, a metal chelate class such as vanadium acetylacetate, cobalt acetylacetate, iron acetylacetonate, an amine class such as aniline, N,N-substituted aniline, N,N-substituted-p-toluidine, 4-(N,N-substituted amino) such as N,N-dimethylaniline, N,N-diethylaniline, p-toluidine, N,N-dimethyl-p-toluidine, N,N-bis(2-hydroxyethyl)-p-toluidine, 4-(N,N-dimethyl amino) benzaldehyde, 4-[N,N-bis(2-hydroxyethyl) amino]benzaldehyde, 4-(N-methyl-N-hydroxyethyl amino) benzaldehyde, N,N-bis(2-hydroxypropyl)-p-toluidine, N-ethyl-m-toluidine, triethanolamine, m-toluidine, diethylenetriamine, pyridine, phenylmorpholine, piperidine, N,N-bis(hydroxyethyl) aniline, di ethanolaniline etc. The additive amount of the curing accelerator is within a range from 0.05 to 5 parts by weight.

As a photoinitiator, it is possible to use a known initiator in the prior art, for example, such as benzophenone series such as benzophenone, benzyl, methylorthobenzoylbenzoate, benzoin ether series such as benzoin alkyl ether, acetophenone series such as benzyl dimethyl ketal, 2,2-diethoxyacetophenone, 2-hydroxy-2-methyl propiophenone, 4-isopropyl-2-hydroxyl-2-methylpropiophenone, 1,1-dichloroacetophenone, thioxanthone series such as 2-chlorothioxanthone, 2-methylthioxanthone, 2-isopropylthioxanthone. The additive amount of the photoinitiator is within a range from 0.1 to 5 parts by weight for 100 parts by weight of the unsaturated polyester resin.

It is possible to prepare an unsaturated polyester resin composition by adding a fiber-reinforced material and/or a filler to the unsaturated polyester resin of the present invention. As a fiber-reinforced material capable of using, for example, it is possible to use a known material in the prior art such as glass fiber, carbon fiber, metal fiber, ceramic fiber, nylon fiber, aramid fiber, vinylon fiber, polyester fiber. In particular, glass fiber is preferable. It is possible to use a various forms of plain fabric, satin weave, bonded textile, mat, roving, chop etc. The proportion of the fiber-reinforced material in the unsaturated polyester resin composition is preferably within a range from 10 to 50% by weight. As a filler, for example, it is possible to use a known material in the prior art, such as calcium carbonate, aluminum hydroxide, magnesium hydroxide, barium sulfate, talc, clay, glass powder, glass bubble, metal powder, quartz sand, gravel, crushed stone etc. The proportion of the filler in the unsaturated polyester resin composition is preferably within a range from 1 to 90% by weight.

Furthermore, a premix molding compound according to the present invention is characterized in that the above unsaturated polyester resin (A) is contained. As a premix molding compound, mention may be made of a sheet molding compound, or a bulk molding compound. That is, it is possible to apply the unsaturated polyester resin of the present invention to a sheet molding compound (hereinafter SMC), and a bulk molding compound (hereinafter BMC) as known in the past. That is, it is a sheet-like or bulk-like molding material made by blending a filler, a fiber-reinforced material, an internal release agent, a low shrinkage agent, a viscosity reducing agent, a thickening agent.

Next, the detailed explanations of the present invention related to polyester resin are described below.

The polyester resin of the present invention is made by two-stage reaction, it is possible to be prepared by obtaining chemical (a) ([Chemical 12]) of the chemical formula (2) at the first-stage reaction, and thereby obtaining polyester at the second-stage reaction as the same manner as the prior art.

The additive amount of the chemical (a) produced by the first-stage is not particularly limited. From a viewpoint that the obtained effect is low in a water resistance or a mechanical property, and an effect of the reduction of environmental load become low, it is preferable to contain 20% by weight or more of the produced compound (a) at the first-stage in the desired polyester raw material.

Next, although as carboxylic acid, alcohol and glycolic acid which are a raw material of a polyester used for the second stage reaction, those of being manufactured thermochemically derived from a fossil fuel according to the prior art, those of being manufactured biochemically derived from a raw material of animals and plants, or those of being manufactured by the thermochemical treatment of a compound produced biochemically derived from a raw material of animals and plants, can be used, it is preferable to use those of being manufactured biochemically derived from a raw material of animals and plants, or those of being manufactured by the thermochemical treatment of a compound produced biochemically derived from a raw material of animals and plants, in the viewpoint of an environmental load and a carbon-neutral.

As carboxylic acids manufactured thermochemically derived from a fossil fuel according to the prior art, mention may be made of phthalic acid, terephthalic acid, isophthalic acid biphenyldicarboxylic acid, naphthalenedicarboxylic acid, 5-tert-butyl-1,3-benzenedicarboxylic acid and an acid anhydride thereof, a derivative such as a lower alkyl ester. Among them, in particular, it is preferable to use at least one selected from the group comprising of terephthalic acid, isophthalic acid, and a derivative thereof. It is possible to use a lower alkyl ester of terephthalic acid and isophthalic acid, as an example of a lower alkyl ester of terephthalic acid and isophthalic acid, although mention may be made of dimethyl terephthalate, dimethyl isophthalate, diethyl terephthalate, diethyl isophthalate, dibutyl terephthalate, dibutyl isophthalate etc., dimethyl terephthalate, dimethyl isophthalate are preferable from a viewpoint of a cost and a handling.

As carboxylic acids manufactured biochemically derived from a raw material of animals and plants, or those of being manufactured by the thermochemical treatment of a compound produced biochemically derived from a raw material of animals and plants, mention may be made of dimer acid, succinic acid, itaconic acid, maleic anhydride, maleic acid, fumaric acid, 2,5-furandicarboxylic acid etc.

It is possible to use it by itself or by the combination of two or more among these carboxylic acids or a lower alkyl ester thereof. Further, it is possible to use a trivalent or more of aromatic polycarboxylic acid too, in a range that dose not impair effects of the present invention. As a trivalent or more of aromatic polycarboxylic acid, mention may be made of trimellitic acid, pyromellitic acid, naphthalenetricarboxylic acid, benzophenonetetracarboxylic acid, biphenyltetracarboxylic acid and an anhydride thereof. It is possible to use it by itself or by the combination of two or more thereof. As a trivalent or more of aromatic polycarboxylic acid, trimellitic anhydride is preferable from a viewpoint of a reactivity.

As alcohols manufactured thermochemically derived from a fossil oil according to the prior art, mention may be made of aliphatic alcohol and etherified diphenol. As an example of aliphatic alcohol, for example, mention may be made of ethylene glycol, 1,2-propanediol, 1,3-propanediol, 1,2-butanediol, 1,3-butanediol, 1,4-butanediol, 2,3-butanediol, 1,4-butenediol, 2-methyl-1,3-propanediol, 1,5-pentanediol, neopentyl glycol, 2-ethyl-2-methylpropane-1,3-diol, 2-butyl-2-ethylpropane-1,3-diol, 1,6-hexanediol, 3-methyl-1,5-pentanediol, 2-ethyl-1,3-hexanediol, 2,4-dimethyl-1,5-pentanediol, 2,2,4-trimethyl-1,3-pentanediol, 1,7-heptanediol, 1,8-octanediol, 1,9-nonanediol, 1,10-decanediol, 3-hydroxy- 2,2-dimethylpropyl-3-hydroxyl-2,2-dimethylpropanoate, diethylene glycol, triethylene glycol, dipropylene glycol etc. As aliphatic alcohol, ethylene glycol, 1,3-propanediol, neopentyl glycol is preferable from a viewpoint of the reactivity with acid and glass-transition temperature of resin.

As alcohols manufactured biochemically derived from a raw material of animals and plants, or manufactured by the thermochemical treatment of a compound produced biochemically derived from a raw material of animals and plants, mention may be made of ethylene glycol, 1,2-propanediol, 1,3-propanediol, 1,4-butanediol, 2,3-butanediol, 2-methyl-1,4-butanediol, glycerin, 2,5-dihydroxymethylfuran.

It is possible to use these aliphatic alcohols by themselves or by the combination of two or more among the above alcohol. Moreover, in the present invention, together with the aliphatic alcohol, further, it is possible to use etherified diphenol. The etherified diphenol is a diol obtained by the addition reaction of alkylene oxide with bisphenol A, as the alkylene oxide, mention may be made of ethylene oxide or propylene oxide, and it is preferable that the average number of moles added is 2 to 16 moles to 1 mole of bisphenol A. It is preferable to use ethylene glycol, 1,2-propanediol, 1,3-propanediol, 1,4-butanediol biochemically produced from the raw material of animals and plants, from a viewpoint of an environmental load and a carbon-neutral. Further, it is possible to use a trivalent or more of polyol too, in a range that dose not impair effects of the present invention. As a trivalent or more of polyol, mention may be made of glycerine, trimethylolethane, trimethylolpropane, pentaerythritol etc., it is possible to use it by itself or by the combination of two or more thereof. As a trivalent or more of polyol, glycerine is preferable from a view point of an environmental load and a carbon-neutral, trimethylolpropane is preferable from a viewpoint of a reactivity.

As other component of the raw material of polyester, it is possible to use alicyclic polycarboxylic acid such as 1,3-cyclohexanedicarboxylic acid, 1,4-cyclohexanedicarboxylic acid, cyclohexanecarboxylic acid, tetrahydrophthalic anhydride, methyltetrahydrophthalic anhydride, endo-methylenetetrahydrophthalic anhydride, halogen-containing dicarboxylic acid such as het acid, tetrabromophthalic anhydride, hydroxycarboxylic acid such as lactic acid, 3-hydroxybutanoic acid, 3-hydroxyl-4-ethoxybenzoic acid too, in a range that dose not impair objects of the present invention.

The polyester resin according to the present invention is prepared by a known common method by using the above compound (a), a predetermined carboxylic acid component, and an alcohol component as a raw material. It is possible to apply any method of a transesterification reaction or a direct esterification reaction as these reaction methods. Further, it is possible to accelerate polycondensation by means of a method of increasing the reaction temperature by applying pressure, a method of reducing pressure or a method of flowing inert gas under normal pressures, too. A reaction at second stage may be conducted without a catalyst, a reaction may be accelerated by using a known common reaction catalyst such as at least one metallic compound selected from the group consisting of antimony, titanium, tin, zinc, aluminum and manganese. It is preferable that the additive amount of these reaction catalysts is within in a range from 0.01 to 1.0 parts by weight for 100 parts by weight of the total amount of carboxylic acid component and alcohol component.

Next, the detailed explanations of the present invention related to a resin particle and an electrophotographic toner are described below. The present invention is made by a resin particle and an electrophotographic toner containing the resin particle. Not only the resin particle of the present invention can be used for an electrophotographic toner, but the water dispersion of the resin particle can be useful as binder components in the field of a paint, an ink, an adhesive agent, and a coating.

The polyester resin which is a raw material of a resin particle and a an electrophotographic toner of the present invention is made by two-stage reaction, it is possible to be prepared by obtaining chemical (a) ([Chemical 12]) of the chemical formula (2) at the first-stage reaction, and thereby obtaining polyester at the second-stage reaction as the same manner as the prior art.

The additive amount of the chemical (a) produced by the first-stage is not particularly limited. From a viewpoint that the obtained effect is low in a water resistance or a mechanical property, and an effect of the reduction of environmental load become low, it is preferable to contain 20% by weight or more of the produced compound (a) at the first-stage in the intended polyester raw material.

Next, although as carboxylic acid, alcohol and glycolic acid which are a raw material of a polyester resin used at the second stage reaction and being a raw material of a resin particle and an electrophotographic toner, those of being manufactured thermochemically derived from a fossil fuel according to the prior art, those of being manufactured biochemically derived from a raw material of animals and plants, or those of being manufactured by the thermochemical treatment of a compound produced biochemically derived from a raw material of animals and plants, can be used, it is preferable to use those of being manufactured biochemically derived from a raw material of animals and plants, or those of being manufactured by the thermochemical treatment of a compound produced biochemically derived from a raw material of animals and plants, in the viewpoint of an environmental load and a carbon-neutral.

As carboxylic acids manufactured thermochemically derived from a fossil fuel according to the prior art, mention may be made of phthalic acid, terephthalic acid, isophthalic acid biphenyldicarboxylic acid, naphthalenedicarboxylic acid, 5-tert-butyl-1,3-benzenedicarboxylic acid and an acid anhydride thereof, a derivative such as a lower alkyl ester. Among them, in particular, it is preferable to use at least one selected from the group comprising terephthalic acid, isophthalic acid, and a derivative thereof. It is possible to use a lower alkyl ester of terephthalic acid and isophthalic acid, as an example of a lower alkyl ester of terephthalic acid and isophthalic acid, although mention may be made of dimethyl terephthalate, dimethyl isophthalate, diethyl terephthalate, diethyl isophthalate, dibutyl terephthalate, dibutyl isophthalate etc., dimethyl terephthalate, dimethyl isophthalate are preferable from a viewpoint of a cost and a handling.

As carboxylic acids manufactured biochemically derived from a raw material of animals and plants, or those of being manufactured by the thermochemical treatment of a compound produced biochemically derived from a raw material of animals and plants, mention may be made of sebacic acid, dimer acid, succinic acid, alkyl succinic acid, alkenyl succinic acid, itaconic acid, maleic anhydride, maleic acid, fumaric acid, 2,5-furandicarboxylic acid etc.

It is possible to use it by itself or by the combination of two or more among these carboxylic acids or a lower alkyl ester thereof. Further, it is possible to use a trivalent or more of aromatic polycarboxylic acid too, in a range that dose not impair effects of the present invention.

As a trivalent or more of aromatic polycarboxylic acid, mention may be made of trimellitic acid, pyromellitic acid, naphthalenetricarboxylic acid, benzophenonetetracarboxylic acid, biphenyltetracarboxylic acid and an anhydride thereof.

It is possible to use it by itself or by the combination of two or more thereof. As a trivalent or more of aromatic polycarboxylic acid, trimellitic anhydride is preferable from a viewpoint of a reactivity.

As alcohols manufactured thermochemically derived from a fossil fuel according to the prior art, mention may be made of aliphatic alcohol and etherified diphenol. As an example of aliphatic alcohol, for example, mention may be made of ethylene glycol, 1,2-propanediol, 1,3-propanediol, 1,2-butanediol, 1,3-butanediol, 1,4-butanediol, 2,3-butanediol, 1,4-butenediol, 2-methyl-1,3-propanediol, 1,5-pentanediol, neopentyl glycol, 2-ethyl-2-methylpropane-1,3-diol, 2-butyl-2-ethylpropane-1,3-diol, 1,6-hexanediol, 3-methyl-1,5-pentanediol, 2-ethyl-1,3-hexanediol, 2,4-dimethyl-1,5-pentanediol, 2,2,4-trimethyl-1,3-pentanediol, 1,7-heptanediol, 1,8-octanediol, 1,9-nonanediol, 1,10-decanediol, 3-hydroxy-2,2-dimethylpropyl-3-hydroxyl-2,2-dimethylpropanoate, diethylene glycol, triethylene glycol, dipropylene glycol etc. As aliphatic alcohol, ethylene glycol, 1,3-propanediol, neopentyl glycol is preferable from a viewpoint of the reactivity with acid and glass-transition temperature of resin.

As alcohol manufactured biochemically derived from a raw material of animals and plants, or manufactured by the thermochemical treatment of a compound produced biochemically derived from a raw material of animals and plants, mention may be made of ethylene glycol, 1,2-propanediol, 1,3-propanediol, 1,4-butanediol, 2,3-butanediol, 2-methyl-1, 4-butanediol, glycerin, 2,5-dihydroxymethylfuran.

It is possible to use these aliphatic alcohols by themselves or by the combination of two or more among the above alcohol. Moreover, in the present invention, together with the aliphatic alcohol, further, it is possible to use etherified diphenol. The etherified diphenol is a diol obtained by the addition reaction of alkylene oxide with bisphenol A, as the alkylene oxide, mention may be made of ethylene oxide or propylene oxide, and it is preferable that the average number of moles added is 2 to 16 moles to 1 mole of bisphenol A. It is preferable to use ethylene glycol, 1,2-propanediol, 1,3-propanediol, 1,4-butanediol biochemically produced from the raw material of animals and plants, from a viewpoint of an environmental load and a carbon-neutral. Further, it is possible to use a trivalent or more of polyol too, in a range that dose not impair effects of the present invention. As a trivalent or more of polyol, mention may be made of glycerine, trimethylolethane, trimethylolpropane, pentaerythritol etc., it is possible to use it by itself or by the combination of two or more thereof. As a trivalent or more of polyol, glycerine is preferable from a viewpoint of an environmental load and a carbon-neutral, trimethylolpropane is preferable from a viewpoint of a reactivity.

As other component of the raw material of polyester, it is possible to use alicyclic polycarboxylic acid such as 1,3-cyclohexanedicarboxylic acid, 1,4-cyclohexanedicarboxylic acid, cyclohexanecarboxylic acid, tetrahydrophthalic anhydride, methyltetrahydrophthalic anhydride, endo-methylenetetrahydrophthalic anhydride, halogen-containing dicarboxylic acid such as het acid, tetrabromophthalic anhydride, hydroxycarboxylic acid such as lactic acid, 3-hydroxybutanoic acid, 3-hydroxyl-4-ethoxybenzoic acid, fatty acid obtained from plant such as flaxseed oil fatty acid, castor oil fatty acid etc., too, in a range that dose not impair objects of the present invention.

The polyester resin according to the present invention is prepared by a known common method by using the above compound (a), a predetermined carboxylic acid component, and an alcohol component as a raw material. It is possible to apply any method of a transesterification reaction or a direct esterification reaction as these reaction methods. Further, it is possible to accelerate polycondensation by means of a method of increasing the reaction temperature by applying pressure, a method of reducing pressure or a method of flowing inert gas under normal pressures, too. A reaction at second stage may be conducted without a catalyst, a reaction may be accelerated by using a known common reaction catalyst such as at least one metallic compound selected from the group consisting of antimony, titanium, tin, zinc, aluminum and manganese. It is preferable that the additive amount of these reaction catalysts is within a range from 0.01 to 1.0 parts by weight for 100 parts by weight of the total amount of carboxylic acid component and alcohol component.

As a method of producing polyester resin according to the present invention other than the above method, it is possible to apply a method of transferring the above compound (a) produced by an another apparatus, and thereby reacting it together with raw materials used at the above second stage in the first stage, or a method of storing the produced above compound (a) in a storage facility, and thereby transferring a necessary amount of them to react it together with raw materials used at the above second stage in one stage.

A preferable softening point of the polyester resin capable of using for the present invention is 90° C. to 160° C. More preferably, it is 100 to 150° C. In the case that a preferable softening point is less than 90° C., a cohesive force of the resin tends to decrease, on the other hand, in the case that a preferable softening point is more than 160° C., a melt flawability and a low-temperature fixability of a toner used for these resin tend to decrease.

There are a fixability and an anti-offset property as a basic performance which is desired for an electrophotographic toner. One of the methods for satisfying both of the competing performances thereof is to mix and use two or more type of polyester resin which a softening point is different from each other, as polyester resin for a toner which is a raw material. In the present invention, in order to satisfy both a fixability and an anti-offset property of the obtained toner, the use of mixing two or more polyester resin having a different softening point is one of preferable embodiments.

In the polyester resin according to the present invention, a glass-transition temperature (Tg) measured from a differential scanning calorimeter (DSC) is 45 to 80° C., more preferably 50 to 75° C. In the case that the Tg is less than 45° C., an anti-blocking property of the toner tends to decrease, a toner aggregation may occur. Furthermore, in the case the Tg is more than 80° C., a low-temperature fixability tends to decrease.

It is necessary to introduce an ionic functional group into the polyester resin used for the present invention in order to enhance a compatibility for water. As an ionic functional group, mention may be made of carboxyl group, sulfonyl group etc. A method of introducing these ionic functional group is not particularly limited, it is possible to introduce them according to a known method in the prior art. For example, mention may be made of a method of introducing carboxyl group by adjusting a total proportion of hydroxyl group for a total amount of carboxyl group in the raw material of polyester resin used for the present invention, a method of introducing carboxyl group by adding acid anhydride such as phthalic anhydride, trimellitic anhydride, pyromellitic anhydride, succinic anhydride during or after the synthesis of polyester resin, a method of using a metal salt of compound with sulfonyl group such as 5-sulfoisophthalic acid etc., as a part of the raw material.

From a viewpoint of the dispersibility for water, in the above polyester resin, an acid value is preferably 3 to 30 mgKOH/g. Further, it is preferably 5 to 20 mgKOH/g. In the case that the above acid value is less than 3 mgKOH/g, the dispersibility for water may tend to decrease. Furthermore, in the case that the above acid value is more than 30 mgKOH/g, a durability of the obtained resin particle or the electrophotographic toner may tend to reduce.

A resin particle and an electrophotographic toner of the present invention can be obtained by a known method in the prior art in the usual manner. For example, in the case of the resin particle, it is possible to obtain it by kneading a resin, and a various type of an additive according to need at a temperature more than a melting point (a softening point) of the resin, and followed by pulverizing and classifying. Furthermore, for example, in the case of the electrophotographic toner, it is possible to obtain it by kneading a resin, a colorant and a various type of an additive according to need at a temperature more than a melting point (a softening point) of the resin, and followed by pulverizing and classifying. However, in order to obtain a toner having a reduced diameter and a narrow particle size distribution which is one of the objects of the present invention, the use of the method for causing the phase inversion as described later is desirable.

The resin particle according to the present invention is characterized in that the resin particle comprises polyester resin wherein a compound shown in the above chemical formula [Chemical 1] (wherein X is an aliphatic or an aromatic residue, Y is a refined rosin residue, a disproportionated rosin residue or a hydrogenated rosin residue, and n=0 to 1 in the formula.) as described above, is an essential component of an alcohol component.

Furthermore, in a preferred embodiment of the resin particle according to the present invention, the invention is characterized in that an average particle diameter of the resin particle is preferably within a range from 0.01 to 1 µm, more preferably within a range from 0.03 to 0.5 µm. In the case that the average particle diameter is more than 1 µm, a particle size distribution of an electrophotographic toner finally obtained thus may tend to become broaden, or storage stability may tend to decrease, such as generation of precipitation during storage of a resin particle dispersion. Moreover, in the case that the average particle diameter is less than 0.1 µm, a resin particle dispersion may tend to become high viscosity, and therefore, it is necessary to reduce a concentration of a solid content, and these makes it possible to reduce a workability.

Furthermore, in a preferred embodiment of the resin particle according to the present invention, the resin particle can be obtained by causing the phase inversion by means of adding a neutralizing agent and an water-based medium into a resin solution made by dissolving the above polyester resin into an organic solvent, and thereby forming an O/W emulsion of resin particle, and further removing the organic solvent from an O/W emulsion of resin particle.

In the present invention, when the polyester is dissolved in the organic solvent, a concentration of a solid content is preferably 30% by weight to 80% by weight. It is preferably 45% by weight to 70% by weight. In the case that it is less than 30% by weight, because it is necessary to use a lot of the organic solvent, it tend to be not desirable from a viewpoint of costs and an environmental point. In the case that the concentration of the solid content is more than 80% by weight, because the viscosity of the solution may tend to become high, and stirring performance of the solution may reduce, it may be not desirable.

As a solvent used during the dissolution of the polyester resin of the present invention, it is possible to use isopropyl alcohol, n-butanol, 2-ethylhexanol, methylethylketone, acetonitrile, dimethylformamide, dimethylacetamide, N-methylpyrrolidone, tetrahydrofuran, 1,4-dioxane, 1,3-dioxane, 1,3-oxirane, methyl cellosolve, ethyl cellosolve, butyl cellosolve, ethyl carbitol, butyl carbitol, propyleneglycol monopropylether, propyleneglycol monobutylether etc. From a viewpoint that the organic solvent can be removed from a resin particle dispersing liquid at short times, in particular, a solvent having an equal to 100° C. or less of a boiling point is preferable, such as methylethylketone, tetrahydrofuran, 1,4-dioxane, 1,3-dioxane, isopropyl alcohol. It is possible to use two or more of these solvent, too.

In the present invention, when a resin particle dispersed in water is obtained with the use of polyester resin having carboxyl group, it is desirable that carboxyl group is neutralized by base, and it is desirable that a timing for addition thereof is from after the polyester resin is dissolved into the organic solvent to until the phase inversion is caused by adding water. It is not preferable that polyester resin, an organic solvent and base are coexisted during a dissolution because it takes a long time for a dissolution. Furthermore, it is not preferable that base is added after causing the phase inversion because it doesn't makes a contribution to a particle formation even if base is added after causing the phase inversion by adding water.

As a base capable of being used as a neutralizing agent, mention may be made of an amine compound such as ammonia, triethylamine, inorganic base series such as sodium hydroxide, potassium hydroxide, sodium carbonate, potassium carbonate etc.

As the amount used of the above base, 0.8 to 1.7 equivalent per a carboxyl group contained in the polyester resin is preferable, more preferably it is within a range from 1.0 to 1.5 equivalent. In the case that it is less than 0.8 equivalent, it may form a precipitation during a water dispersion process because it is impossible to render a sufficient hydrophilicity to a resin. Furthermore, in the case that it is more than 1.7 equivalent, a particle size distribution tends to broaden.

A water dispersion of the resin particle of the present invention can be obtained by adding the above base to the polyester resin dissolved into the solvent, and neutralizing, and thereby adding water to cause the phase inversion. It is desirable that a temperature during the phase inversion is equal to a room temperature or more, and equal to a boiling point of the organic solvent or base or less.

It is preferable that the solvent is removing from the water dispersion of the resin particle of the present invention after the neutralization and the phase inversion. The organic solvent can be removing by a common method such as application of heat, reduced pressure treatment etc. A residual amount of the organic solvent in the water dispersion of the resin particle of the present invention is desirably equal to 2% or less from a viewpoint of keeping a stability as dispersion. More preferably, it is equal to 1% or less. The removed organic solvent can be used for the dissolution of the resin again.

Next, an electrophotographic toner of the present invention will be explained. An electrophotographic toner of the present invention is an electrophotographic toner containing the resin particle of the present invention, mention may be made of an electrophotographic toner made by using the resin particle of the present invention as it is. Furthermore, since it is possible to obtain water dispersion of the resin particle having a smaller particle diameter than a toner size, mention may be made of an electrophotographic toner made by using a resin particle obtained by mixing a dispersion of other resin particle made separately according to need, and controlling appropriately the conditions such as a temperature, a pH, an electrolytic concentration of the obtained dispersion, and thereby making a particle with a toner size by aggregating and coalescencing the resin particle dispersion followed by filtering and drying.

An electrophotographic toner according to the present invention is characterized in that the electrophotographic toner comprises at least polyester resin and colorant, and comprises a resin particle comprising the polyester resin wherein a compound shown in the above chemical formula [chemical 3] (wherein X is an aliphatic or an aromatic residue, Y is a refined rosin residue, a disproportionated rosin residue or a hydrogenated rosin residue, and n=0 to 1 in the formula.), is an essential component of an alcohol component. Therefore, essentially, it is possible to apply the explanation regarding the resin particle of the present invention as mentioned above to the following electrophotographic toner of the present invention.

Furthermore, an electrophotographic toner according to the present invention is characterized in that an average particle diameter of the resin particle is within a range from 0.01 to 1 μm.

Furthermore, in a preferred embodiment of the electrophotographic toner according to the present invention, the invention is characterized in that the toner comprises a resin particle obtained by causing the phase inversion by means of adding a neutralizing agent and an water-based medium into a resin solution made by dissolving the polyester resin into an organic solvent, and thereby forming an O/W emulsion of a resin particle, and further removing the organic solvent from a O/W emulsion of a resin particle.

Furthermore, in a preferred embodiment of the electrophotographic toner according to the present invention, the invention is characterized in that the compound is obtained by the addition reaction of one or more selected from the group consisting of a refined rosin, a disproportionated rosin, and a hydrogenated rosin, to an epoxy group of a compound having two epoxy group in one molecule and shown in the above chemical formula [chemical 4] (wherein X is an aliphatic or an aromatic residue, and n=0 to 1 in the formula.).

Furthermore, in a preferred embodiment of the electrophotographic toner according to the present invention, the invention is characterized in that the compound shown in the above [chemical 7] is contained at 20 percent by weigh or more as a raw material of polyester.

Furthermore, in a preferred embodiment of the electrophotographic toner according to the present invention, the invention is characterized in that the neutralizing agent is contained at 0.8 to 1.7 equivalent per equivalent of a carboxyl group contained in the polyester resin.

A method of aggregating and coalescencing the resin particle dispersion will further be explained as follows. It is possible to obtain a resin particle by mixing a resin particle dispersion of the present invention into an water-based medium with a colorant particle dispersion separately prepared or a colored resin particle dispersion separately prepared, and thereby aggregating and coalescencing a resin particle dispersion by adding a reverse neutralizing agent to reduce a surface potential of the resin particle, with a colorant particle or a colored resin particle to obtain a colored resin particle dispersion having more larger average particle diameter, and after that, a particle is filtered to dry. In this case, it is also possible to use an additive such as a wax etc., a magnetic powder, a charge control agent together with the above colorant, and it is also possible to aggregate and coalescence them by adding a resin particle dispersion containing an additive, a magnetic powder, a charge control agent etc.

Further, as one embodiment of the present invention, it is also possible to apply a method of dissolving or dispersing a colorant and/or other additive by adding them at the same time or at a given point in time during process when polyester resin of the present invention is dissolved into the organic solvent.

Furthermore, the organic solvent may be removing after the aggregation and coalescence between the resin particle and the colorant or the colored resin particle is carried out. An average particle diameter of a fine particle existing in each dispersion used here is preferably within a range from 0.01 to 1 μm, from a viewpoint of a storage stability and a handling, and more preferably within a range from 0.03 to 0.5 μm. An average particle diameter of the colored resin particle (a toner particle) after the aggregation and coalescence is preferably within a range from 3 to 15 μm, more preferably within a range from 4 to 10 μm form a viewpoint of a quality of image.

As a method of aggregating and coalescencing the resin particle or the colorant particle etc., mention may be made of a method of heating a dispersion after a salting agent made of an alkali metal salt or an alkaline earth metal salt is added into a water dispersion existing the resin particle or the colorant particle etc.

As a salting agent used here, mention may be made of chlorine salt, bromine salt, iodine salt, carbonate, sulphate etc., of potassium, sodium, magnesium, calcium, barium, aluminum etc.

The filtration/washing process is a process being carry out both a filtration treatment for filtrating the toner particle from dispersing liquid of a toner particle obtained by the above process, and a washing treatment for removing a remaining surfactant and salting agent etc., from the filtrated toner particle. At this moment, as a method of the filtration treatment, although mention may be made of a centrifugal separation method, a method of filtration under reduced pressure carried out by using a nutsche etc., a filtering method carried out by using a filter press, it is not limited to these.

In the dry process, as a drier used here, although mention may be made of a spray drier, a vacuum-freeze drier, a vacuum drier etc., it is not limited to these. In the case that each of the dried toner particle is aggregating each other, it is also possible to pulverize the aggregate by a crushing equipment such as a jet mill, a henschel mixer etc.

As a separately prepared water dispersion of a colorant or a separately prepared water dispersion of a colored resin particle, for example, mention may be made of a water dispersion wherein the colorant is treated by emulsification using a surfactant etc., a water dispersion wherein a colorant and a resin is heat melted, and thereby dispersing them into water containing a dispersing agent, a water dispersion wherein a resin dispersed the colorant is dissolved into an organic solvent, and thereby adding water to cause the phase inversion.

In the electrophotographic toner of the present invention, it is possible to use any colorant which is known in the prior art. As an example of these colorants, mention may be made of a colorant for black such as carbon black, aniline black, acetylene black, iron black etc., a colorant for color, such as various types of dyes and pigments compound such as phthalocyanine series, rhodamine series, quinacridone series, triallylmethane series, anthraquinone series, azo series, diazo series, methane series, allylamide series, thioindigo series, naphthol series, isoindolinone series, diketopyrrolopyrrole series, benzimidazolone series etc., and metal-complex compounds thereof and lake compounds thereof. It is possible to use it by itself or by the combination of two or more among the above colorant.

A positive or negative charge control agent may be added to the electrophotographic toner of the present invention according to need. An representative example of a charge control agent, in a black toner, mention may be made of nigrosine for a positive charge toner, monoazo dye metal salt for a negative charge toner etc. In a full color toner, mention may be made of quaternary ammonium salts, imidazole metal-complexes for a positive charge toner, salicylic acid metal-complexes, organic boron salts for a negative charge toner etc.

A release agent may be added to the electrophotographic toner of the present invention. As the release agent, mention may be made of synthetic waxes such as low-molecular-weight polypropylene, polyethylene etc., natural waxes such as paraffin wax, carnauba wax, rice wax, montan wax, beeswax etc.

Furthermore, in an electrophotographic toner, a magnetic powder may be internally added according to need, to obtain a magnetic toner. As a magnetic powder internally added to these toners, it is possible to use any of powder such as alloys, an oxides, a compound containing a ferromagnetic element used in manufacture of a magnetic powder in the prior art. As an example of these magnetic powder, mention may be made of a powder of a compound made be a magnetic iron oxide such as magnetite, maghemite, ferrite, or a bivalent metal and an iron oxide, a powder of metals such as iron, cobalt, nickel, or a powder of a metal alloy such as aluminum, cobalt, copper, lead, magnesium, tin, zinc, antimony, beryllium, bismuth, cadmium, calcium, manganese, selenium, titanium, tungsten, vanadium and a mixture of these powders.

The electrophotographic toner of the present invention can be used as two component developer by mixing a carrier. As a carrier capable of using together with the toner of the present invention, it is possible to use any carrier which is known in the prior art. As a usable carrier, for example, mention may be made of the magnetic powders such as iron powder, ferrite powder, nickel powder or a glass bead etc. These carrier particles may be coated with a resin etc., on these surfaces. As a resin for coating a surface of the carrier, mention may be made of styrene-acrylate copolymer, styrene-methacrylate copolymer, acrylate copolymer, methacrylate copolymer, fluorine containing resin, silicon containing resin, polyamide resin, ionomer resin, polyphenylenesulfide resin etc., and a mixture thereof. Among them, fluorine containing resin, silicon containing resin is particularly preferable because a spent toner is formed in a less amount.

An external additive may be added to the electrophotographic toner of the present invention in order to improve a flowability etc. As an example of these external agent, mention may be made of an inorganic fine particle such as silica, alumina, titania, a fluorocarbon type of resin fine particle such as polyvinylidene fluoride, polytetrafluoroethylene, a fine particle of acrylate resin, styrene acrylate resin produced by an emulsion polymerization.

An average particle diameter of the toner particle in the electrophotographic toner of the present invention is preferably within a range from 3 to 15 μm, from a viewpoint of a quality of image, an average particle diameter of the toner is more preferably within a range from 4 to 10 μm. Moreover, a measurement for an average particle diameter and a particle size distribution of the toner, for example can be carried out by using the Coulter Counter.

At this moment, toner properties will be explained. In the embodiment of the present invention, an average particle diameter of the toner is preferably within a range from 3 to 15 μm, is more preferably within a range from 4 to 10 μm. In the case that the particle diameter is too small, not only it is lack of stability of manufacturing, but it is difficult to control an internal structure, and chargeability become inadequate, and developability tends to decrease. In the case that the particle diameter is too large, resolution of image tends to decrease.

Moreover, in the embodiment of the present invention, a volume average particle size distribution index (GSDv) is preferably 1.30 or less. Moreover, a ratio (GSDv/GSDp) of a volume average particle size distribution index (GSDv) and a number average particle size distribution index (GSDp) is preferably 0.95 or more. In the case that a volume average particle size distribution index (GSDv) is more than 1.30, resolution of image may deteriorate, and further in the case that a ratio (GSDv/GSDp) of a volume average particle size distribution index (GSDv) and a number average particle size distribution index (GSDp) is less than 0.95, a toner chargeability may deteriorate, a scattering and a fogging of the toner may occur, as a result, these makes is possible to induce image defects.

Moreover, in the embodiment of the present invention, an average particle diameter of the toner, the value of the above volume average particle size distribution index (GSDv) and number average particle size distribution index (GSDp) was measured and calculated as follows. First of all, the toner particle distribution measured using a Coulter Multisizer II (Beckman Coulter, Inc.) is divided into particle size ranges (channels), and cumulative distribution curves are drawn beginning at smaller particle sizes at the point for the volume and number of each of the toner particle. On these curves, the particle size at the point where the accumulated value reaches 16% is defined as the volume average particle size D16v or the number average particle size D16p respectively, and the particle size at the point where the accumulated value reaches 50% is defined as the volume average particle size D50v or the number average particle size D50p respectively. In the similar way, the particle size at the point where the accumulated value reaches 84% is defined as the volume average particle size D84v or the number average particle size D84p respectively. In this case, the value of the above volume average particle size distribution index (GSDv) is defined as D84v/D16v, and the number average particle size distribution index (GSDp) is defined as D84p/D16p. By using these relational expression, the volume average particle size distribution index (GSDv) and the number average particle size distribution index (GSDp) can be calculated.

The electrophotographic toner of the present invention can be used to any developing method or developing apparatus for developing an electrostatic charge image formed by an electrophotography, an electrostatic recording or an electrostatic printing method etc. such as a copying machine, a printer, or a facsimile etc. in the prior art.

EXAMPLE

At first, the present invention related to the unsaturated polyester resin will be concretely explained in more detail with reference to Examples 1 to 5, but the invention is not intended to be interpreted as being limited to Examples. Moreover, in what follows, the number of parts shows parts by weight, a raw material without description which is from a biomass shows a raw material derived from a fossil fuel.

Synthetic Example 1

A New Unsaturated Polyester Resin 1046 g of Bisphenol A type of resin as an epoxy resin of the compound (a), 1990 g of disproportionated rosin (an acid value is a 156 mgKOH/g, from a biomass), 1.5 g of triphenylphosphine as the reaction catalyst were added into a stainless-steal reaction vessel with a stirring device, a heating device, a thermometer, a fractionally distilling equipment, nitrogen gas introduction tube to react under nitrogen atmosphere, with stirring at 180° C. for 5 hours, and to confirm that the acid value is less than 5 mgKOH/g to obtain a compound (a). A reaction formula is as follows. That is, as shown in the below [chemical 13], first of all, Bisphenol A type of epoxy resin was reacted with disproportionated rosin to synthesize the compound (a).

[Chemical 13]

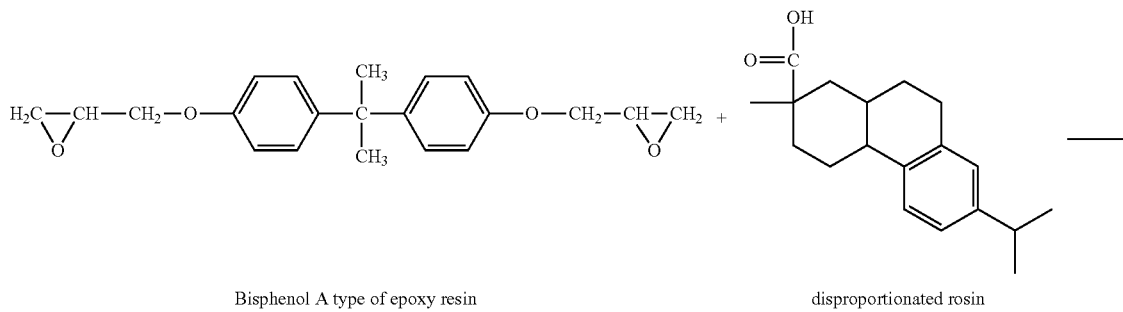

Bisphenol A type of epoxy resin + disproportionated rosin

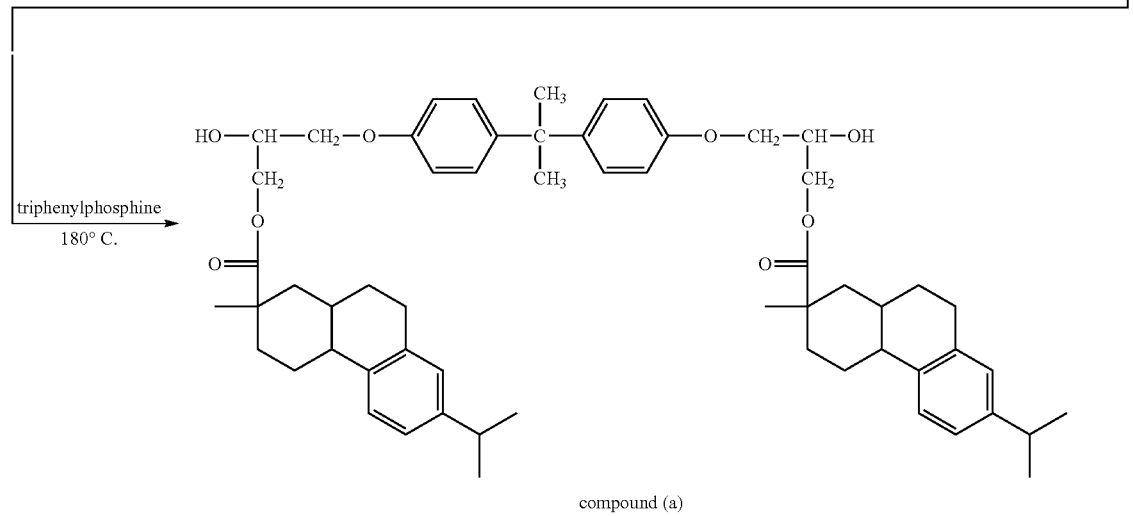

compound (a)

Next, 307 g of ethylene glycol (from a biomass), 549 g of 1,2-propanediol, 1356 g of maleic anhydride were added into a vessel to allow a polycondensation reaction at 210° C. of a reaction temperature, for 14 hours, to terminate the reaction when a desirable acid value is obtained, and thereby adding 2692 g of styrene monomer to obtain 65% of nonvolatile material of unsaturated polyester resin (A-1) (See table 1 regarding synthesis and formulation). The reaction formula is as follows. That is, as shown in the below [chemical 14], the reaction was carried out in the conventional manner by using compound (a) as alcohol component of the raw material of the unsaturated polyester.

[Chemical 14]

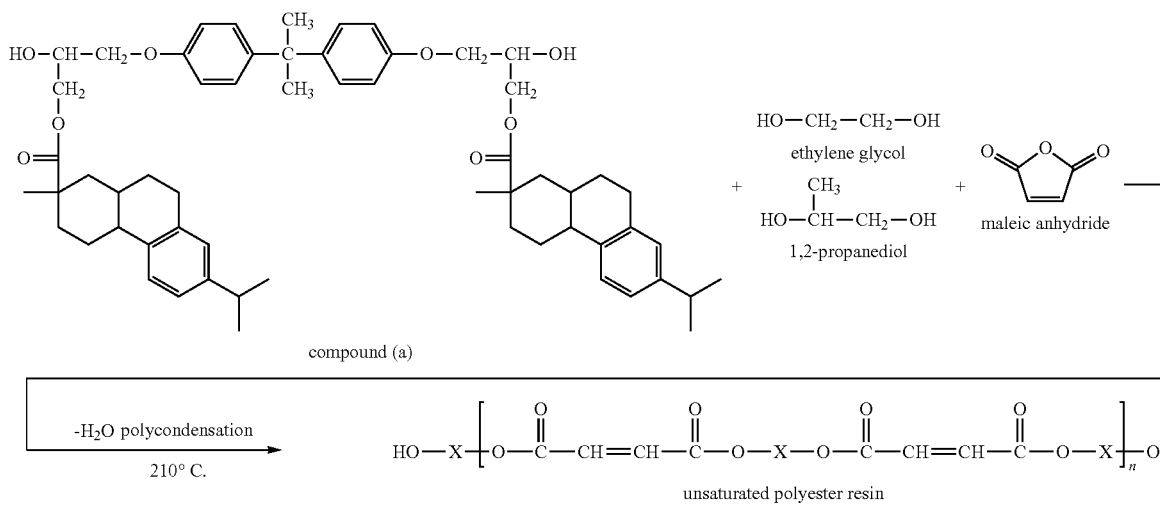

unsaturated polyester resin

-continued

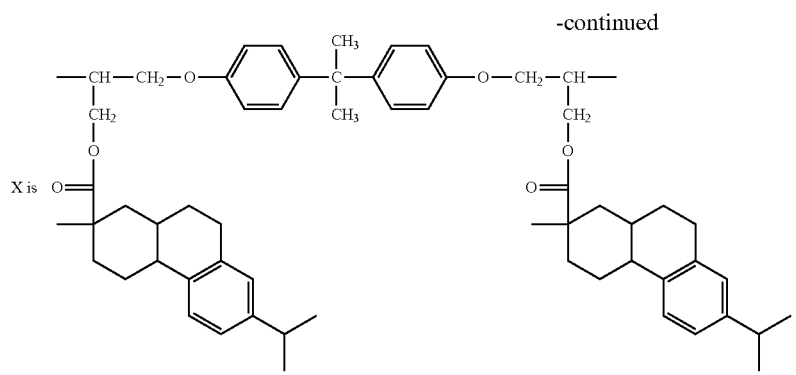
X is and 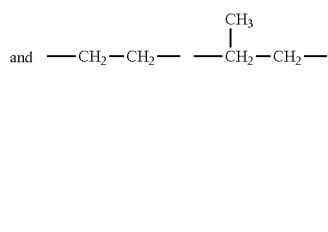

Synthetic Examples 2 and 3

Table 1 shows synthesis composition and formulation. A numeric value shows parts by weight.

In the table 1, in addition to synthesis composition and formulation, a ratio in the raw material of compound (a), an acid value of a synthesis end point, a content amount of a raw material derived from a biomass were shown. A content

TABLE 1

| | | unsaturated polyester resin | | | | |
|---|---|---|---|---|---|---|
| | | A-1 | A-2 | A-3 (reference) | B-1 (comparison) | B-2 (comparison) |
| glycol component | compound (a) (biomass 66%) | 3036 | 2128 | 879 | — | — |
| | ethylene glycol (from biomass) | 307 | 361 | 663 | — | — |
| | ethylene glycol | — | — | — | 683 | 336 |
| | 1,2-propanediol(from biomass) | 549 | 956 | 1320 | — | — |
| | 1,2-propanediol | — | — | — | 1424 | 1030 |
| | neopentylglycol | — | — | — | — | — |
| saturated acid comp. | terephthalic acid | — | — | — | 2286 | 1124 |
| unsaturated acid comp. | maleic anhydride | 1356 | 1901 | 2618 | 1349 | 1991 |
| weight ratio in raw material of compound(a) | | 57.9% | 39.8% | 16% | — | — |
| acid value of end point mgKOH/g (solid content) | | 5.6 | 12.8 | 8.1 | 5.9 | 5.10 |
| content of raw material from biomass (% by weight) | | 36.9 | 35.1 | 35.1 | 0 | 0 |

The unsaturated polyester resin (A-2), (A-3: reference example) was synthesized in the same manner as Synthetic example 1, except that it is a formulation shown in table 1.

Synthetic Example 4

Synthetic Example of the Unsaturated Polyester Resin for Comparison 683 g of ethylene glycol, 1425 g of 1,2-propanediol as an alcohol component of the unsaturated polyester resin, 2286 g of terephthalic acid as acid component and 4.7 g of tetra-n-butyl titanate as a reaction catalyst were added into a stainless-steal reaction vessel with a stirring device, a heating device, a thermometer, a fractionally distilling equipment, nitrogen gas introduction tube to allow a polycondensation reaction under nitrogen atmosphere, with stirring at 220° C. for 14 hours. After that, 1349 g of maleic anhydride was added to terminate the reaction when a desirable acid value is obtained, and thereby adding 2692 g of styrene monomer to obtain 65% of nonvolatile material of unsaturated polyester resin (B-1).

Synthetic Example 5

Synthetic Example of the Unsaturated Polyester Resin for Comparison

The unsaturated polyester resin (B-2) were synthesized in the same manner as Synthetic example 4, except that it is a formulation shown in table 1.

amount of biomass was calculated from the following formula.

The content amount of the raw material from the biomass=(a charging amount of the biomass component)×100/(a total charging amount−a theoretical generated water amount)

However, a charging amount of the biomass component is calculated as follows. That is, in the case that the biomass component is acid, a 17.01 which is molecular weight corresponding to OH is subtracted from these molecular weight, and in the case that the biomass component is alcohol, a 1.01 which is molecular weight corresponding to H is subtracted from these molecular weight, it was calculated by multiplying each subtracted value by the number of moles.

Example 1

An Evaluation of Physical Property by Means of Cast Molding Plate

To the predetermined synthesized each unsaturated polyester resin was added and mixed 0.5% of a commercially available 6% cobalt naphthenate as a curing accelerator, to the resin was added and mixed 1% of 55% methylethylketone peroxide to be cured. A cast molding plate was made according to JIS K 6919, section 5.2.3. Test was carried out under the condition of curing wherein after it was cured at room temperature for 24 hours, a post cure was carried out wherein a condition is at 80° C.×2 hours and at 120° C.×2 hours. A tensile strength and tensile modulus thereof of a cast molding plate was measured according to JIS K 7113, a flexural strength and a flexural modulus was measured according to JIS K 7203, a Barcol hardness was measured according to JIS K 6919, an Izod impact was measured according to JIS K 7110, a heat distortion temperature and water absorption was measured according to JIS K 6911, a molding shrinkage was measured according to JIS K 6919, respectively, and a result of this was shown in table 2. The table 2 shows a result of physical property of a cast molding plate.

TABLE 2

| | | unsaturated polyester resin | | | | |
|---|---|---|---|---|---|---|
| | | (Example 1-1) A-1 | (Example 1-2) A-2 | (Reference 1-1) A-3 | (Comparison 1-2) B-1 | (Comparison 1-3) B-2 |
| tensile strength | MPa | 66 | 72 | 71 | 68 | 88 |
| tensile modulus | GPa | 4.1 | 3.9 | 3.8 | 3.8 | 3.9 |
| tensile elongation | % | 2.1 | 2.4 | 2.6 | 2.3 | 0.4 |
| flexural strength | MPa | 98 | 113 | 100 | 116 | 65 |
| flexural modulus | GPa | 4.2 | 3.9 | 3.9 | 4.2 | 3.6 |
| Izod | kJ/m$^2$ | 10 | 12 | 11 | 11 | 8 |
| heat distortion temperature | ° C. | 116 | 137 | 142 | 67 | 133 |
| Barcol hardness | — | 51 | 49 | 46 | 47 | 49 |
| water absorption 1(%) | % | 0.16 | 0.17 | 0.31 | 0.19 | 0.40 |
| water absorption 2(%) | % | 0.31 | 0.39 | 0.54 | 0.74 | 0.77 |
| molding shrinkage | % | 6.1 | 6.3 | 8.3 | 7.8 | 8.9 |

Example 2

An Evaluation of Physical Property by Means of Laminated Plate

To the synthesized each unsaturated polyester resin is added and mixed 0.5% of a commercially available 6% cobalt naphthenate as a curing accelerator, and then, to the resin is added and mixed 1% of 55% methylethylketone peroxide. Next, a laminated plate having 3 mm of thickness was made by impregnating and laminating the above resin on 450 g/m$^2$ of the prepared chopped strand mat 3 ply. Test was carried out under the condition of curing wherein after it was cured at room temperature for 24 hours, a post cure was carried out wherein a condition is at 80° C.×2 hours and at 120° C.×2 hours. A tensile strength and tensile modulus thereof of a laminated plate was measured according to JIS K 7113, a flexural strength and a flexural modulus was measured according to JIS K 7171, an Izod impact was measured according to JIS K 7110, respectively, and a result of this was shown in table 3. The table 3 shows a result of physical property of a laminated plate plate.

TABLE 3

| | | unsaturated polyester resin | | | | |
|---|---|---|---|---|---|---|
| | | (Example 2-1) A-1 | (Example 2-2) A-2 | (Reference 2-1) A-3 | (Comparison 2-2) B-1 | (Comparison 2-3) B-2 |
| tensile strength | MPa | 108 | 116 | 109 | 103 | 118 |
| tensile modulus | GPa | 8.2 | 8.3 | 8.4 | 8.3 | 8.9 |
| flexural strength | MPa | 192 | 186 | 178 | 188 | 154 |
| flexural modulus | GPa | 8.2 | 8.1 | 7.9 | 7.5 | 8.2 |

Example 3

An Evaluation of Physical Property by Means of SMC

A SMC was produced by formulating 800 parts of the synthesized each unsaturated polyester resin (A-2, comparison B-2) with 200 parts of 30% polystyrene solution as a low profile agent, 2 parts of BYK972 (BYK-Chemie) as a reducing viscosity agent, 50 parts of zinc stearate as a release agent, 1800 parts of calcium carbonate as a filler, 780 parts of a chopped glass as a glass fiber, 20 parts of Perhexyl HI (NOF corporation) as a radical initiator, 20 parts of magnesium oxide as a thickening agent. The obtained SMC is press molded at 145° C. of mold temperature, for 6 minutes to obtain SMC molded article. Each physical property of SMC was measured in the same manner as Examples 1 and 2, a molding shrinkage was calculated from a difference between a molded dimension and a dimension of the obtained molded article. Furthermore, a boiling test was carried out by confirming a surface condition by a visual check after a face of SMC was immersed at 90° C. of a hot water for 800 hours. A result of this was shown in table 4. Table 4 shows a result of physical property of SMC.

TABLE 4

| | | unsaturated polyester resin blended in SMC | |
|---|---|---|---|
| | | (Example 3-1) A-2 | (Comparison 3-1) B-2 |
| tensile strength | MPa | 79 | 72 |
| tensile modulus | GPa | 12.7 | 12.2 |
| tensile elongation | % | 0.9 | 1.0 |
| flexural strength | MPa | 182 | 183 |
| flexural modulus | GPa | 13.1 | 12.9 |
| Izod | kJ/m$^2$ | 76 | 58 |
| heat distortion temperature | ° C. | 250° C. or more | 250° C. or more |
| molding shrinkage | % | 0.12 | 0.17 |
| condition after boiling test | | with no swelling | with swelling |

Example 4

An Evaluation of Physical Property by Means of BMC

A BMC was produced by formulating 1000 parts of the synthesized each unsaturated polyester resin (A-2, comparison B-2) with 5 parts of polystyrene pellet as a low profile agent, 40 parts of zinc stearate as a release agent, 2800 parts of aluminum hydroxide as a filler, 100 parts of a chopped glass as a glass fiber, 10 parts of Perhexa 3M (NOF corporation) as a radical initiator, 8 parts of magnesium oxide as a thickening agent to use a kneader. The obtained BMC was press molded at 135° C. of mold temperature, for 8 minutes to obtain BMC molded article having a thickness of 5 mm. Each physical property of BMC was measured in the same manner as Examples 1 and 2, a molding shrinkage was calculated from a difference between a molded dimension and a dimension of the obtained molded article.

Example 5

Comparison of Amount of Carbon-Dioxide Emission

As an index of an environmental load, an amount of carbon dioxide generated when 1 kg of the unsaturated polyester resin is wasted by combustion, was calculated. However, carbon dioxide from a biomass raw material was counted out an emission in consideration of a concept of carbon-neutral. Table 5 shows a result of physical property of BMC. Furthermore, table 6 shows a result of calculation, that is, an emission of carbon dioxide when 1 kg of the unsaturated polyester resin is combusted and discarded. In the table 6, carbon dioxide from a biomass raw material is counted out an emission in consideration of a concept of carbon-neutral.

TABLE 5

|  |  | unsaturated polyester resin blended in BMC | |
|---|---|---|---|
|  |  | (Example 4-1) A-2 | (Comparison 4-1) B-2 |
| tensile strength | MPa | 58 | 56 |
| tensile modulus | GPa | 11.9 | 11.8 |
| tensile elongation | % | 0.3 | 0.3 |
| Izod | kJ/m$^2$ | 5.1 | 4.9 |
| molding shrinkage | % | 0.24 | 0.37 |
| condition after boiling test |  | with no swelling | with swelling |

TABLE 6

| | polyester resin | | | | |
|---|---|---|---|---|---|
| | (Example 5-1) A-1 | (Example 5-2) A-2 | (Reference 5-1) A-3 | (Comparison 5-2) B-1 | (Comparison 5-3) B-2 |
| CO2 emission (kg/1 kg) | 1.87 | 1.89 | 2.05 | 2.58 | 2.56 |

It is recognized that the unsaturated polyester resin of the present invention and a FRP molded article with the use of the resin of the present invention has, from tables 2 to 5, an equivalent mechanical and mechanical property, a low water absorption, and a low shrinkage at curing comparing with these of the unsaturated polyester resin of the prior art and a FRP molded article with the use of the resin of the prior art. Furthermore, it is recognized that if a concept of carbon-neutral is applied, the unsaturated polyester resin of the present invention is a low environmental load material since an emission of carbon dioxide at the time of the combustion is less than that of the unsaturated polyester resin using a fossil fuel based raw material of the prior art from table 6.

Next, the present invention related to a new polyester resin will be concretely explained in more detail with reference to Examples, but the invention is not intended to be interpreted as being limited to Examples. Moreover, in what follows, the number of parts shows parts by weight, a raw material without description which is from a biomass shows a raw material from a fossil fuel.

Synthetic Example 6

A New Polyester Resin and a Resin Synthetic Example for Comparison Example 1316 g of Bisphenol A type of resin as an epoxy resin of the compound (a), 2506 g of disproportionated rosin (acid value is a 156 mgKOH/g, from a biomass), 1.9 g of triphenylphosphine as the reaction catalyst were added into a stainless-steal reaction vessel with a stirring device, a heating device, a thermometer, a fractionally distilling equipment, nitrogen gas introduction tube to react under nitrogen atmosphere, with stirring at 180° C. for 5 hours, and to confirm that the acid value is less than 5 mgKOH/g to obtain a compound (a). A reaction formula is as follows. That is, as shown in the below [Chemical 15], first of all, Bisphenol A type of epoxy resin was reacted with disproportionated rosin to synthesize the compound (a).

[Chemical 15]

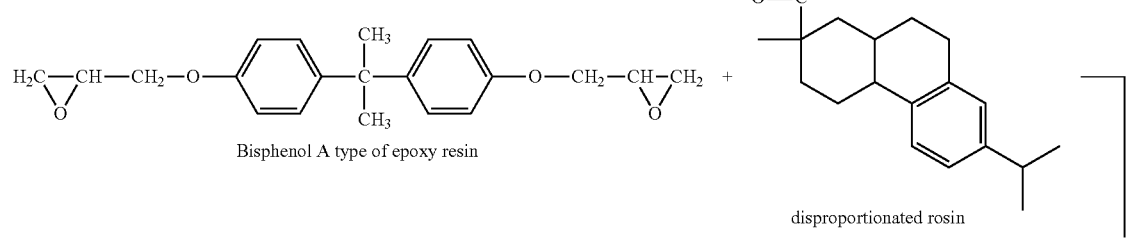

Bisphenol A type of epoxy resin disproportionated rosin

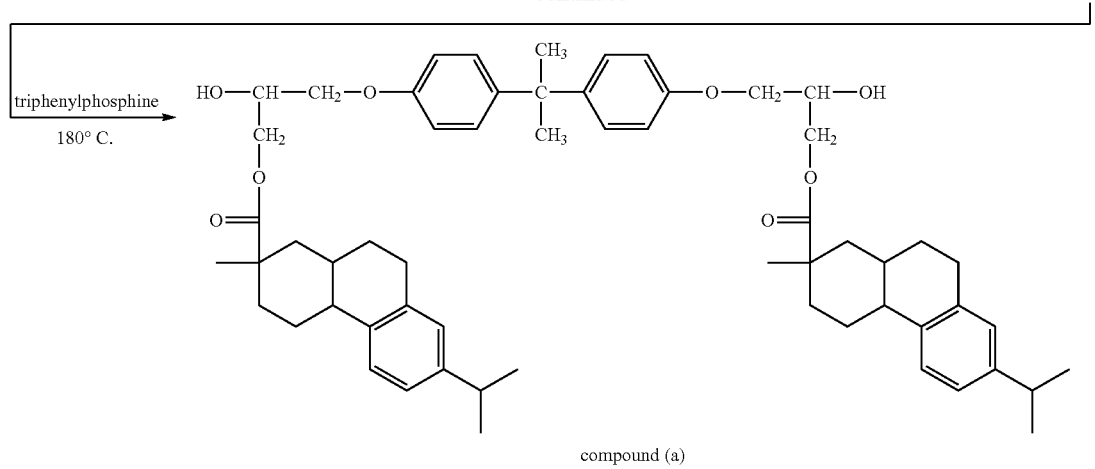

compound (a)

Next, 273 g of ethylene glycol (from a biomass), 1157 g of terephthalic acid were added into a vessel to allow a polycondensation reaction at 250° C. of a reaction temperature, for 14 hours, to terminate the reaction when a desirable acid value is obtained, and thereby obtaining polyester resin (A-4) (See table 7 regarding synthesis and formulation). The reaction formula is as follows. That is, as shown in the below [Chemical 16], the reaction was carried out in the conventional manner by using compound (a) as alcohol component of the raw material of the polyester.

[Chemical 16]

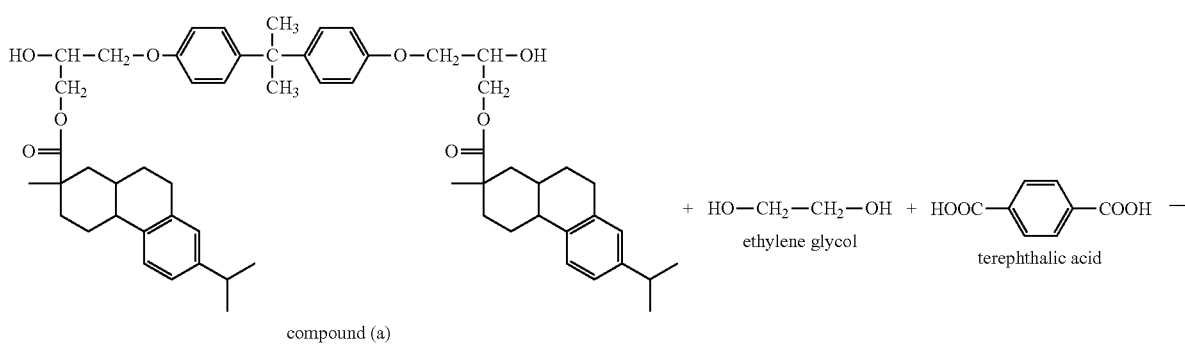

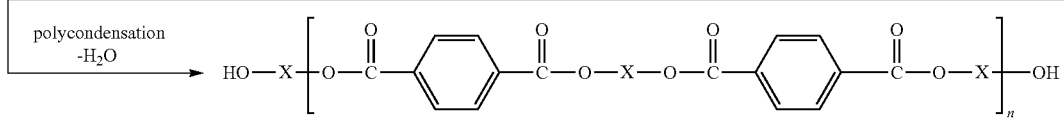

X is

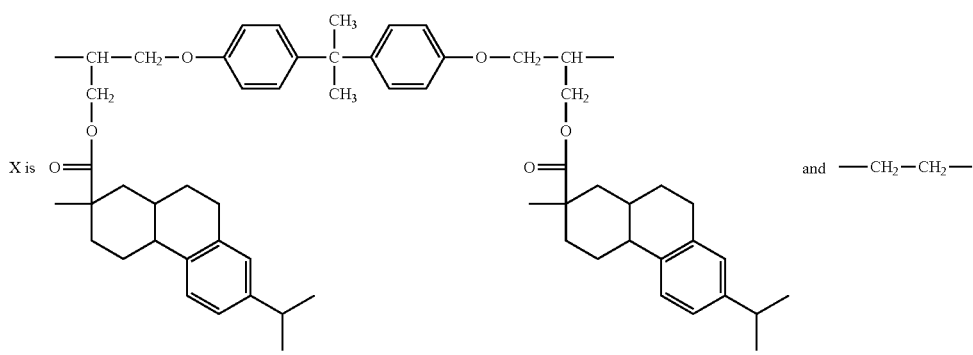

and —$CH_2$—$CH_2$—

Synthetic Examples 7 and 8

Table 7 shows synthesis composition and formulation. A numeric value shows parts by weight.

TABLE 7

|  |  | polyester resin | | | | |
| --- | --- | --- | --- | --- | --- | --- |
|  |  | A-4 | A-5 | A-6 (Reference) | B-3 (Comparison) | B-4 (Comparison) |
| glycol component | compound (a) (biomass 66%) | 3822 | 2689 | 508 | — | — |
|  | ethylene glycol (from biomass) | 273 | 479 | 841 | — | — |
|  | ethylene glycol | — | — | — | 1082 | 562 |
|  | 1,2-propanediol(from biomass) | — | 238 | 654 | — | — |
|  | neopentylglycol | — | — | — | 813 | — |
|  | Adduct of BPA and 2 moles of EO | — | — | — | — | 2435 |
| Acid comp. | terephthalic acid | 1157 | 2035 | 3572 | 3966 | 2558 |
| weight ratio in raw material of compound(a) | | 80% | 59% | 17% | — | — |
| acid value of end point | | 1.8 | 2.3 | 2.3 | 1.9 | 2.2 |
| hydroxyl equivalent (g/eq) | | 1910 | 1800 | 1770 | 1740 | 1790 |
| content of raw material from biomass (% by weight) | | 50.1 | 39.9 | 22.0 | 0 | 0 |

In the table, adduct of BPA and 2 moles of EO means adduct of 2 moles of ethylene oxide to bisphenol A The polyester resin (A-5), (A-6: reference example) was synthesized in the same manner as Synthetic example 6, except that it is a formulation shown in table 7.

Synthetic Example 9

Synthetic Example of the Polyester Resin for Comparison 813 g of neopentyl glycol as alcohol component of polyester resin, 1082 g of ethylene glycol, 3966 g of terephthalic acid as acid component and 4.7 g of tetra-n-butyl titanate as a reaction catalyst were added into a stainless-steal reaction vessel with a stirring device, a heating device, a thermometer, a fractionally distilling equipment, nitrogen gas introduction tube to allow a polycondensation reaction under nitrogen atmosphere, with stirring at 250° C. for 16 hours, to terminate the reaction when a desirable acid value is obtained, and thereby obtaining a polyester resin (B-3).

The polyester resin (B-4) was synthesized in the same manner as Synthetic example 8, except that it is a formulation proportion shown in table 7.

In the table 7, in addition to synthesis composition and formulation, a ratio of compound (a), an acid value of a synthesis end point, hydroxyl equivalent were shown. A content amount of biomass was calculated from the following formula.

> The content amount of the raw material from the biomass=(a charging amount of the biomass component)×100/(a total charging amount−a theoretical generated water amount)

However, a charging amount of the biomass component is calculated as follows. That is, in the case that the biomass component is acid, a 17.01 which is molecular weight corresponding to OH is subtracted from these molecular weight, and in the case that the biomass component is alcohol, a 1.01 which is molecular weight corresponding to H is subtracted from these molecular weight, it was calculated by multiplying each subtracted value by the number of moles.

Synthetic Examples 11

A Synthetic Example of Urethane Acrylate Using New Polyester 1000.0 g of isobornyl acrylate, 58.2 g of 2-hydroxy acrylate, 54.6 g of isophorone diisocyanate, 885.9 g of polyester resin (A-5), 1.0 g of hydroquinone as a polymerization inhibitor, and 0.2 g of dibutyltin dilaurate as a catalyst were added into a stainless-steal reaction vessel with a stirring device, a heating device, a thermometer, a fractionally distilling equipment, nitrogen gas introduction tube to react, with stirring at 100° C. for 6 hours under air atmosphere. After it was confirmed that an isocyanate group was disappeared with an IR, to obtain a polyester urethane acrylate resin (U-1)(please see table 8 regarding synthesis composition and formulation. Table 8 shows a synthesis composition and formulation. In the table, a numeric value shows parts by weight.

TABLE 8

|  |  | polyester urethane acrylate resin | |
| --- | --- | --- | --- |
|  |  | U-1 | U-2 (Comparison) |
| polyester resin | A-5 | 885.9 | — |
|  | B-3 | — | 882.5 |
| isophorone diisocyanate | | 54.6 | 56.3 |
| 2-hydroxy acrylate | | 58.2 | 60.0 |
| isobornyl acrylate | | 1000.0 | 1000.0 |
| hydroquinone as a polymerization inhibitor | | 1.0 | 1.0 |
| dibutyltin dilaurate as a catalyst | | 0.2 | 0.2 |

Synthetic Example 12

The polyester urethane acrylate resin (U-2) was synthesized in the same manner as Synthetic example 11, except that it is a formulation proportion shown in table 8.

Example 6

A water absorption and an impact resistance of a polyester plate and a disk were measured as an evaluation of the polyester resin by itself. The result of measurement was shown in table 9. Table 9 shows a result of water absorption and an impact resistance.

TABLE 9

| | polyester resin | | | | |
|---|---|---|---|---|---|
| | (Example 6-1) A-4 | (Example 6-2) A-5 | (Reference 6-1) A-6 | (Comparison 6-2) B-3 | (Comparison 6-3) B-4 |
| water absorption(%) | 0.17 | 0.18 | 0.30 | 0.37 | 0.34 |
| impact value(cm) | 75 | 60 | 45 | 40 | 50 |

A Water Absorption: To a water bath at 23° C. were immersed a 5 cm square and a thickness of 3 mm of polyester plate, and thereby polling out after 24 hours to calculate from both weight of before and after the immersion.
An Impact Resistance A 4 cm diameter and a thickness of 5 mm of a disk was used as a test sample, when a steel ball having a 9.53 mm diameter and a 3.5 g of weight is dropped, a height until the test sample was crushed, was measured.

Example 7

As an evaluation of the powder coating, according to below formulation the powder coating was made and thereby carrying out electrostatic coating to obtain a coating film. As an evaluation, a molecular weight distribution before and after melt kneading was measured, existence or nonexistence of a molecular chain by hydrolysis and water resistance (moisture resistance) were examined. A result of the evaluation was shown in table 10. The table 10 shows an evaluation of performance of the coating film by the powder coating.

TABLE 10

| | polyester resin contained in composition for the powder coating | | | | |
|---|---|---|---|---|---|
| | (Example 7-1) A-4 | (Example 7-2) A-5 | (Reference 7-1) A-6 | (Comparison 7-2) B-3 | (Comparison 7-3) B-4 |
| molecular weight change before and after melt kneading | ○ | ○ | Δ | Δ | Δ |
| condition of coating film after water resistance test | ○ | ○ | Δ | X | Δ |

A Molecular Weight Change Before and after Melt Kneading:
A molecular weight change before and after melt kneading was measured by a gel permeation chromatography (GPC). A molecular weight change before and after melt kneading: with no changes ○, a little bit of changes Δ, with changes X.
A Humidity Resistance:
According to JIS K5600-7-2, a test was carried out under the conditions of at 50±1° C. of a temperature, at 95% or more of a relative humidity of a position of test specimen existing in a humid box for 500 hours. A change of a coating film after humidity resistance test: with no swelling and with no gloss reduction ○, with no swelling and with gloss reduction Δ, with swelling and with gloss reduction X.
Formulation of Powdered Paint
87 parts of each synthesized polyester, 13 parts of ε-caprolactam blocked isophoronediisocyanate based curing agent "Vestagon B1530" made by Evonik Industries, 50 parts of rutile type titanium dioxide pigment "TIPAQUE CR-90" made by Ishihara Sangyo Kaisha, Ltd., 0.5 parts of benzoin, 1.0 parts of a silicone based leveling agent. 0.3 parts of an organic tin compound based curing catalyst, at first, were dry blended by a FM20C/I type of Mitsui Henschel mixer, and then melt kneaded with the use of PLK46 type of Buss ko-kneader, and after cooling them, and thereby pulverizing and classifying with 150 mesh of a metal gauze to obtain a powdered coating.

The powder coating made as mentioned above, was coated on a steel plate treated with zinc phosphate with the use of an electrostatic powder coating machine to obtain a curing coating film having 50 to 60 μm of a film thickness by baking at 180° C. for 20 minutes.

Example 8

As an evaluation of an electrophotographic developer, a resin composition was made according to the below formulation. As an evaluation, a molecular weight distribution before and after melt kneading was measured, existence or nonexistence of a molecular chain by hydrolysis and water resistance (moisture resistance) of the electrophotographic developer were examined. A result of the evaluation was shown in table 11. The table 11 shows an evaluation of performance of the electrophotographic developer.

TABLE 11

| | polyester resin contained in composition for the electrophotographic developer | | | | |
|---|---|---|---|---|---|
| | (Example 8-1) A-4 | (Example 8-2) A-5 | (Reference 8-1) A-6 | (Comparison 8-2) B-3 | (Comparison 8-3) B-4 |
| molecular weight change before and after melt kneading | ○ | ○ | Δ | X | Δ |
| weight change by moisture | ○ | ○ | Δ | X | Δ |

A Molecular Weight Change Before and after Melt Kneading:
A molecular weight change before and after melt kneading was measured by a gel permeation chromatography (GPC). A molecular weight change before and after melt blending: with no changes ○, a little bit of changes Δ, with changes X.
A Hygroscopic Property:
The electrophotographic developer was put under the conditions of at 50±1° C. of an incubator temperature, at 85% of a relative humidity, and a weight change was examined after 500 hours. The weight change by a hygroscopic property: with little or nothing of changes ○, with change Δ, with a large changes X.
Formulation of the Electrophotographic Developer
93 parts of each synthesized polyester, 4 parts of a copper phthalocyanine pigment, and 3 parts of paraffin wax (76° C. of a melting point) were mixed, and thereby melt kneading at 130° C., pulverizing and classifying to obtain a negatively-charged particle having 7.4 μm of an average particle diameter. Next, to 100 parts of this particle was added and mixed 1.0 parts of a silica fine powder treated by dimethyldichlorosilane to obtain an electrophotographic developer.

Example 9

100 parts of polyester urethane acrylate resin were blended 3 parts of trimethylolpropane triacrylate as a reactive diluent and 2 parts of a photoinitiator (Irgacure 184) and thereby obtaining a coating film having 100 µm of thickness by means of a ultraviolet curing to measure water absorption at normal temperature. Furthermore, a shrinkage was calculated by a relative density. A result of the measurement was shown in table 12. The table 12 shows an evaluation of polyester urethane acrylate.

TABLE 12

|  | urethane acrylate resin contained in UV cure resin composition | |
| --- | --- | --- |
|  | (Example -9) U-1 | (Comparison -9) U-2 |
| a water absorption(%) | 0.16 | 0.29 |
| a shrinkage(%) | 4.1 | 6.2 |

A Water Absorption

To a water bath of 23° C. was immersed polyester urethane acrylate curing material having a square of 3 cm and a thickness of 100 µm, and took it from a bath after 24 hours and thereby being calculated from a weight before and after immersion.

A Shrinkage

A shrinkage was calculated from a difference between a fluid relative density and a relative density of a cured material.

Example 10

As an index of an environmental load, an amount of carbon dioxide generated when the polyester resin is wasted by combustion, was calculated. However, carbon dioxide from a biomass raw material was counted out an emission in consideration of a concept of carbon-neutral. A result of calculation was shown in table 13. The table 13 shows an emission of carbon dioxide when 1 kg of the polyester resin is combusted and discarded.

TABLE 13

|  | polyester resin | | | | |
| --- | --- | --- | --- | --- | --- |
|  | (Example 10-1) A-4 | (Example 10-2) A-5 | (Reference 10-1) A-6 | (Comparison 10-2) B-3 | (Comparison 10-3) B-4 |
| CO2 emission (kg/1 kg) | 1.21 | 1.31 | 1.65 | 2.33 | 2.53 | carbon dioxide from a biomass raw material was removed from an emission in consideration of a concept of carbon-neutral.

The polyester resin of the present invention, the powder coating, the electrophotographic developer, and polyester urethane acrylate using the invention have a good performance on a water resistance, a shrinkage, a mechanical property compared with that of the polyester resin using a raw material derived from fossil fuel of the prior art, from the tables 9 to 12. Furthermore, it is recognized that the polyester resin of the present invention is a material reduced an environmental load, because an emission of carbon dioxide when combusted is less than a polyester resin using a raw material derived from fossil fuel of the prior art from the table 13.

Next, although the present invention related to the resin particle etc., will be concretely explained in more detail with reference to Examples as follows, but the invention is not intended to be interpreted as being limited to these Examples. Moreover, in what follows, the number of parts shows parts by weight.

An acid value, a glass-transition temperature (Tg), a softening temperature (Tm) are as follows.

(An Acid Value)

An acid value means a milligram number of potassium hydroxide which is needed to neutralize an acid group containing in 1 g of a sample.

(A Glass-transition Temperature)

A glass-transition temperature means a temperature of the intersecting point between a extension line of a base line which is equal to the Tg or less, and a tangential line of an endothermic curve which is located adjacent to the Tg, when it is measured at 20° C./minutes of a heating rate with the use of a differential scanning calorimeter (made by SII Nano-Technology Inc., DSC-6220).

(A Softening Temperature)

A softening temperature means a temperature when an amount of descent of a plunger of a flow tester is 4 mm, in the case that it is measured under the conditions of 30 kg of a load, 1 mm of a nozzle diameter, 10 mm of a nozzle length, at 80° C. of preheating for 5 minutes, at 3° C./minutes of a heating rate, as 1 g of an amount of sample with the use of elevated flow tester (made by Shimadzu Corporation CFT-500D).

(A Content Amount of the Raw Material from the Biomass)

A content amount of the raw material of the biomass was calculated from the following formula.

The content amount of the raw material from the biomass=(a charging amount of the biomass component)×100/(a total charging amount−a theoretical generated water amount)

However, a charging amount of the biomass component is calculated as follows. That is, in the case that the biomass component is acid, a 17.01 which is molecular weight corresponding to OH is subtracted from these molecular weight, and in the case that the biomass component is alcohol, a 1.01 which is molecular weight corresponding to H is subtracted from these molecular weight, it was calculated by multiplying each subtracted value by the number of moles.

(A Method of Measuring a Particle Size of the Resin Particle and a Particle Size Distribution)

It was measured by using a laser diffraction particle size distribution analyzer (LA-700 made by Horiba, Ltd.). A sample which becomes dispersion liquid state containing about 2 g as a solid content is prepared, and to this is added an ion-exchange water to be about 40 mL. This is added to a cell until it become a suitable concentration, after about 2 minutes, it is measured when the concentration in cell become almost stable. The volume average particle diameter for each of obtained channels is accumulated beginning at the smaller volume average particle diameter, and the point where the accumulated value reaches 50% is defined as the volume average particle diameter (median size). A span as an index of the extent of the particle size distribution is shown by using a number wherein a value of 10% of diameter is subtracted from that of 90% of diameter and divided at median size.

(A Method of Measuring a Particle Size of the Toner Particle and a Particle Size Distribution)

A Coulter Multisizer II type (Beckman Coulter, Inc.) was used and as an electrolyte, ISOTON-II (Beckman Coulter, Inc.) was used. The method of measuring involves adding from 0.5 to 50 mg of the measuring sample to a surfactant as the dispersant (2 ml of a 5% aqueous solution of a sodium alkylbenzenesulfonate is preferred), and then adding this sample to 100 ml of the above electrolyte. The electrolyte containing the suspended sample was subjected to dispersion treatment for about 1 minutes in an ultrasonic disperser, according to a Coulter Multisizer II, with the use of 100 µm of aperture as aperture diameter, a particle size distribution from 2 to 60 μm of a particle was measured to obtain a volume average particle size distribution and a number average particle size distribution. The number of particles to be measured was 50,000. Further, a toner particle size distribution was calculated by the following method. Namely, previously measured particle size distribution was divided into particle size ranges (channels), and a volume cumulative distribution curve was drawn beginning at the smaller particle sizes. On this curve, the particle size at the point where the accumulated number of particles reaches 16% is defined as D16p, and the particle size at the point where the accumulated particle volume reaches 50% is defined as D50v. Further, the particle size at the point where the accumulated number of particles reaches 84% is defined as D84p. In the present invention, the volume average particle size was the D50v, and the number average particle size distribution index on the low particle size side GSDp-low was calculated by the following formula.

$$GSDp\text{-low} = \{(D84p)/(D16p)\}^{0.5} \quad \text{Formula}$$

(A Concentration of a Remaining Organic Solvent in the Resin Particle Dispersion Liquid)

With the use of a gas chromatograph (GC-9A made by Shimadzu Corporation), a packed column (G-300 made by chemical evolution and research instrument, Japan), 150° C. of an injection temperature, 150° C. of a detector temperature, 1-acetoxy-2-methoxyethane as an internal standard material, a concentration of the organic solvent was obtained by directly inducing those of a resin particle dispersion diluented with an ion-exchange water.

(A storage Stability)

The resin particle dispersion liquid was allowed at room temperature for 90 days, a storage stability was assessed by existence or non existence of a generation of precipitates. ○: with no precipitates, Δ: precipitates was slightly found, X: precipitates was clearly found.

(A production of a New Polyester Resin A-7)

1175 g of Bisphenol A type of resin as an epoxy resin of the compound (a), 2281 g of disproportionated rosin (an acid value is a 156 mgKOH/g, from a biomass), 1.7 g of triphenylphosphine as the reaction catalyst were added into a stainless-steal reaction vessel with a stirring device, a heating device, a thermometer, a fractionally distilling equipment, nitrogen gas introduction tube to react under nitrogen atmosphere, with stirring at 180° C. for 5 hours, and to confirm that the acid value is less than 5 mgKOH/g to obtain a compound (a). A reaction formula is as follows. That is, as shown in the below [Chemical 17], first of all, Bisphenol A type of epoxy resin was reacted with disproportionated rosin to synthesize the compound (a).

[Chemical 17]

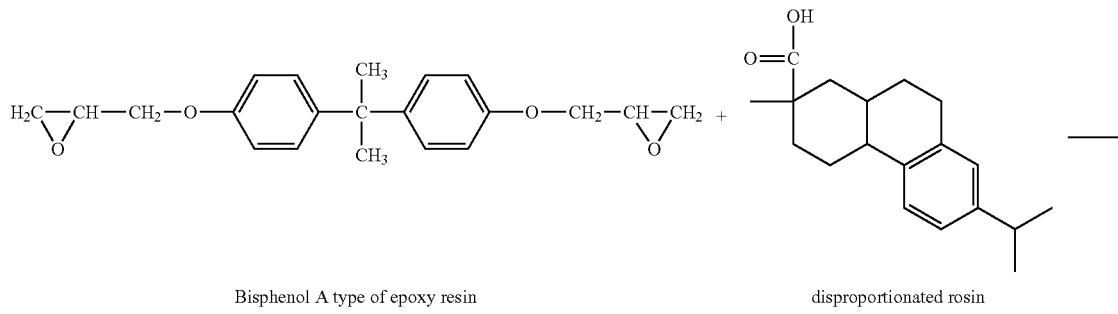

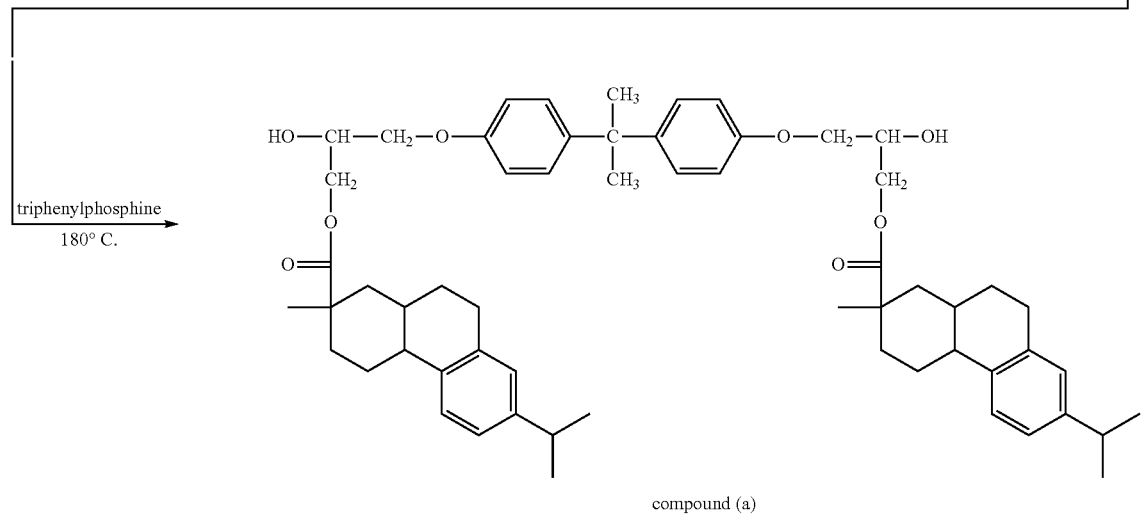

Next, 382 g of ethylene glycol (from a biomass), 1481 g of terephthalic acid were added into a vessel to allow a polycondensation reaction at 250° C. of a reaction temperature, for 14 hours, to terminate the reaction when a desirable acid value is obtained, and thereby obtaining polyester resin (A-7). The characteristic value of the obtained resin is shown in table 14. The reaction formula is as follows. That is, as shown in the below [Chemical 18], the reaction was carried out in the conventional manner by using compound (a) as alcohol component of the raw material of the polyester.

Next, 282 g of 1,2-propanediol (from a biomass), 923 g of isophthalic acid, 359 g of dimer acid (an acid value is a 193

[Chemical 18]

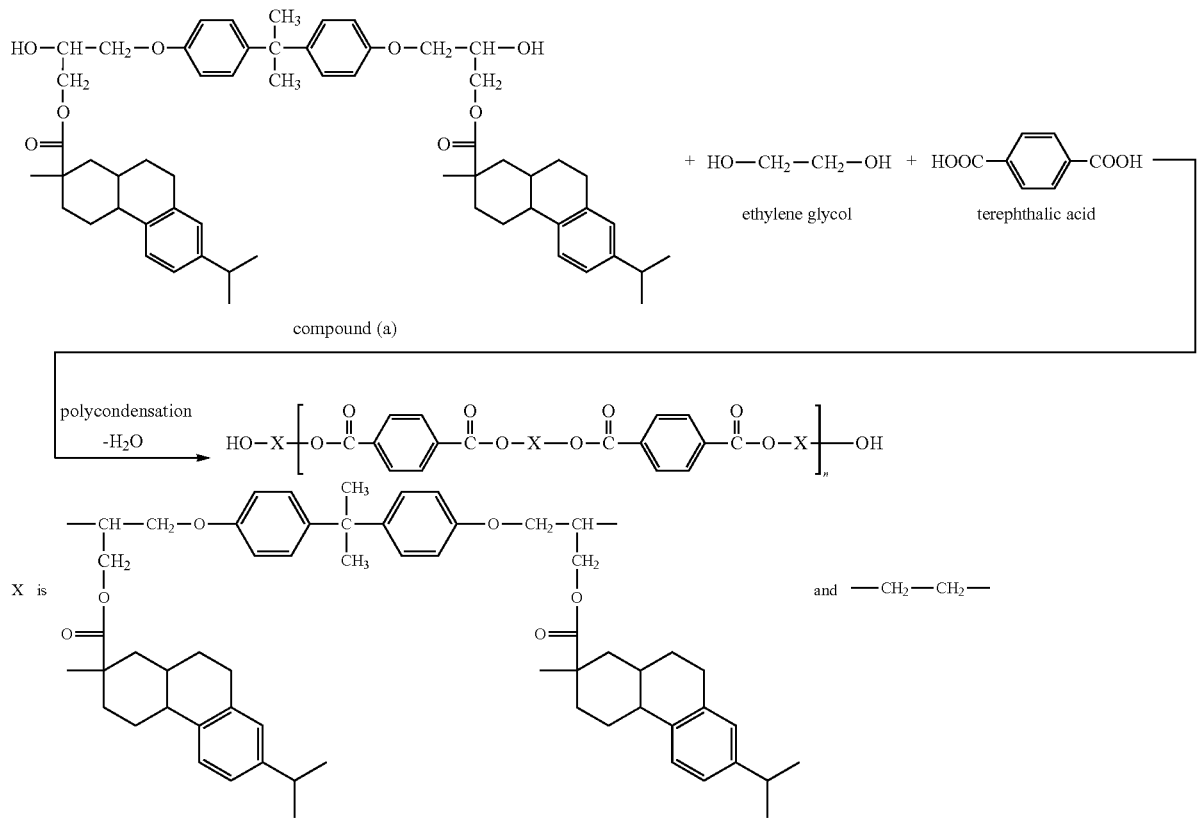

(A Production of a New Polyester Resin A-8)

1095 g of Bisphenol A type of resin as an epoxy resin of the compound (a), 2023 g of disproportionated rosin (an acid value is a 156 mgKOH/g, from a biomass), 1.6 g of triphenylphosphine as the reaction catalyst were added into a stainless-steal reaction vessel with a stirring device, a heating device, a thermometer, a fractionally distilling equipment, nitrogen gas introduction tube to react under nitrogen atmosphere, with stirring at 180° C. for 5 hours, and to confirm that the acid value is less than 5 mgKOH/g to obtain a compound (a).

Next, 624 g of 1,3-propanediol (from a biomass), 802 g of terephthalic acid, and 802 g of isophthalic acid were added into a vessel to allow a polycondensation reaction at 250° C. of a reaction temperature, for 10 hours, to terminate the reaction when a desirable acid value is attained, and thereby obtaining polyester resin (A-8). The characteristic value of the obtained resin is shown in table 14.

(A Production of a New Polyester Resin A-9)

1284 g of Bisphenol A type of resin as an epoxy resin of the compound (a), 2372 g of disproportionated rosin (an acid value is a 156 mgKOH/g, from a biomass), 1.8 g of triphenylphosphine as the reaction catalyst were added into a stainless-steal reaction vessel with a stirring device, a heating device, a thermometer, a fractionally distilling equipment, nitrogen gas introduction tube to react under nitrogen atmosphere, with stirring at 180° C. for 5 hours, and to confirm that the acid value is less than 5 mgKOH/g to obtain a compound (a).

mgKOH/g, from a biomass) were added into a vessel to allow a polycondensation reaction at 250° C. of a reaction temperature, for 15 hours, to terminate the reaction when a desirable acid value is attained, and thereby obtaining polyester resin (A-9). The characteristic value of the obtained resin is shown in table 14.

(A Production of a Polyester Resin for Comparison B-5)

590 g of ethylene glycol as an alcohol component of polyester resin raw material, 2530 g of adduct of 2 moles of propylene oxide to Bisphenol A, as an acid component, 1308 g of terephthalic acid, 700 g of isophthalic acid, 378 g of trimellitic anhydride, and 1.7 g of tetra-n-butyltitanate as the reaction catalyst were added into a stainless-steal reaction vessel with a stirring device, a heating device, a thermometer, a fractionally distilling equipment, nitrogen gas introduction tube to react under nitrogen atmosphere, with stirring at 250° C. for 12 hours, to terminate the reaction when a desirable acid value is attained, and thereby obtaining polyester resin (B-5). The characteristic value of the obtained resin is shown in table 14.

(A Production of a Polyester Resin for Comparison B-6)

1082 g of ethylene glycol as an alcohol component of polyester resin raw material, 813 g of 1,3-propanediol, 3966 g of terephthalic acid as an acid component, and 1.7 g of tetra-n-butyltitanate as the reaction catalyst were added into a stainless-steal reaction vessel with a stirring device, a heating device, a thermometer, a fractionally distilling equipment, nitrogen gas introduction tube to react under nitrogen atmosphere, to allow a polycondensation reaction under nitrogen atmosphere, with stirring at 250° C. for 14 hours, to terminate the reaction when a desirable acid value is attained, and thereby obtaining polyester resin (B-6). The characteristic value of the obtained resin is shown in table 14.

(A Production of a Polyester Resin for Comparison B-7)

562 g of ethylene glycol as an alcohol component of polyester resin raw material, 2435 g of adduct of 2 moles of ethylene oxide to Bisphenol A, as an acid component, 1023 g of terephthalic acid, 1535 g of isophthalic acid, and 1.7 g of tetra-n-butyltitanate as the reaction catalyst were added into a stainless-steal reaction vessel with a stirring device, a heating device, a thermometer, a fractionally distilling equipment, nitrogen gas introduction tube to react under nitrogen atmosphere, to allow a polycondensation reaction under nitrogen atmosphere, with stirring at 250° C. for 13 hours, to terminate the reaction when a desirable acid value is attained, and thereby obtaining polyester resin (B-7). The characteristic value of the obtained resin is shown in table 14.

sphere within the system was replaced with nitrogen gas. Next, with stirring in the system, polyester resin was heated at 60° C. and dissolved. To this was added as a neutralizing agent, 2.58 parts by weight of 10% ammonia water and then with the use of constant rate pump with stirring 240 parts by weight of ion-exchange water was added at 4.8 g/minutes of velocity. When in an emulsification system, a creamy white was found and an agitating viscosity was reduced, the emulsification was terminated.

Next, to the reaction vessel was equipped a pressure reducing device with vacuum pump, and thereby stirring at 50° C. of an internal temperature of the reaction bath, under reduced pressure of 6 kPa [abs] within the reaction bath. When a total amount of a remaining solvent in the resin particle dispersion is 1000 ppm or less, it was a end point of the termination of reaction to allow the internal pressure of the reaction bath to a normal pressure, and with stirring to cool down to room temperature. The characteristic value of the obtained resin particle dispersion (1) is shown in table 15.

TABLE 14

| | | polyester resin | | | | | |
|---|---|---|---|---|---|---|---|
| | | A-7 | A-8 | A-9 | B-5 (Comparison) | B-6 (Comparison) | B-7 (Comparison) |
| glycol comp. | compound (a) (biomass 66%) | 3456 | 3118 | 3657 | — | — | — |
| | ethylene glycol (from biomass) | 382 | — | — | — | — | — |
| | ethylene glycol | — | — | — | 590 | 1082 | 562 |
| | 1,2-propanediol (from biomass) | — | — | 282 | — | — | — |
| | 1,2-propanediol | — | — | — | — | 813 | — |
| | 1,3-propanediol (from biomass) | — | 624 | — | — | — | — |
| | Adduct of BPA and 2 moles of EO | — | — | — | — | — | 2435 |
| | Adduct of BPA and 2 moles of PO | — | — | — | 2530 | — | — |
| acid comp. | terephthalic acid | 1481 | 802 | — | 1308 | 3966 | 1023 |
| | isophthalic acid | — | 802 | 923 | 700 | — | 1535 |
| | anhydrous trimellitic acid | — | — | — | 378 | — | — |
| | dimer acid (from biomass) | — | — | 359 | — | — | — |
| weight ratio in raw material of compound (a) | | 69% | 62% | 73% | — | — | — |
| acid value | | 8.7 | 8.1 | 10.5 | 13.5 | 7.8 | 9.4 |
| A glass-transition temperature | | 61.4 | 59.6 | 61.3 | 64.1 | 59.1 | 63.0 |
| A softening temperature | | 143.9 | 113.9 | 117.0 | 142.7 | 112.6 | 111.9 |
| content of raw material from biomass (% by weight) | | 52.5 | 53.0 | 60.3 | 0 | 0 | 0 |

In the table, adduct of BPA and 2 moles of EO means adduct of 2 moles of ethylene oxide to bisphenol A
In the table, adduct of BPA and 2 moles of PO means adduct of 2 moles of propylene oxide to bisphenol A Example 11

After 70 parts by weight of a rough grinding polyester resin (A-7), 30 parts by weight of a rough grinding polyester resin (A-8) were added to a vessel with a stirring device, a condenser and a thermometer, 60 parts by weight of methylethyl ketone and 20 parts by weight of isopropyl alcohol were added. Nitrogen gas was supplied with and an ambient atmo- Examples 12 to 16

The resin particle dispersion (2) to (6) was produced in the same manner as Example 11, except that it is a formulation proportion shown in table 15. The characteristic value of the obtained resin particle dispersion is shown in table 15.

TABLE 15

| | | composition | | | | | | characteristic value | | | |
|---|---|---|---|---|---|---|---|---|---|---|---|
| instance | resin particle dispersion No. | polyester resin | | solvent composition | | amount of neutralizing agent | equivalent weight of neutralizing agent for total carboxyl group | median size (nm) | span | content of organic solvent (% by weight) | storage stability |
| example 11 | (1) | A-7 70 parts | A-8 30 parts | MEK 60 parts | IPA 20 parts | 2.58 parts | 1.00 | 141 | 0.88 | 0.05 | ○ |
| 12 | (2) | A-7 70 parts | A-8 30 parts | MEK 60 parts | IPA 20 parts | 3.23 parts | 1.25 | 259 | 1.16 | 0.06 | ○ |

TABLE 15-continued

| instance | resin particle dispersion No. | polyester resin | | solvent composition | | amount of neutralizing agent | equivalent weight of neutralizing agent for total carboxyl group | median size (nm) | span | content of organic solvent (% by weight) | storage stability |
|---|---|---|---|---|---|---|---|---|---|---|---|
| 13 | (3) | A-7 70 parts | A-8 30 parts | MEK 60 parts | IPA 20 parts | 3.87 parts | 1.50 | 272 | 1.15 | 0.05 | ○ |
| 14 | (4) | A-7 70 parts | A-8 30 parts | MEK 70 parts | IPA 10 parts | 2.58 parts | 1.00 | 150 | 1.02 | 0.03 | ○ |
| 15 | (5) | A-7 50 parts | A-8 50 parts | MEK 60 parts | IPA 20 parts | 2.55 parts | 1.00 | 132 | 0.85 | 0.04 | ○ |
| 16 | (6) | A-7 70 parts | A-9 30 parts | MEK 60 parts | IPA 20 parts | 2.80 parts | 1.00 | 178 | 0.99 | 0.05 | ○ |

Comparison Examples 1 to 6

The resin particle dispersion (7) to (12) was produced in the same manner as Example 11, except that it is a formulation proportion shown in table 16. The characteristic value of the obtained resin particle dispersion is shown in table 16.

TABLE 16

| instance | | resin particle dispersion No. | polyester resin | | solvent composition | | amount of neutralizing agent | equivalent weight of neutralizing agent for total carboxyl group | median size (nm) | span | content of organic solvent (% by weight) | storage stability |
|---|---|---|---|---|---|---|---|---|---|---|---|---|
| Comparison example | 1 | (7) | B-5 70 parts | B-6 30 parts | MEK 60 parts | IPA 20 parts | 3.57 parts | 1.00 | bad dispersion | — | — | X |
| | 2 | (8) | B-5 70 parts | B-6 30 parts | MEK 60 parts | IPA 20 parts | 4.47 parts | 1.25 | 1351 | 1.85 | 0.22 | X |
| | 3 | (9) | B-5 70 parts | B-6 30 parts | MEK 60 parts | IPA 20 parts | 5.36 parts | 1.50 | 183 | 1.15 | 0.15 | Δ |
| | 4 | (10) | B-5 50 parts | B-6 50 parts | MEK 60 parts | IPA 20 parts | 4.84 parts | 1.50 | 250 | 1.23 | 0.23 | X |
| | 5 | (11) | B-5 70 parts | B-7 30 parts | MEK 60 parts | IPA 20 parts | 4.65 parts | 1.25 | 632 | 2.03 | 0.37 | Δ |
| | 6 | (12) | B-5 70 parts | B-7 30 parts | MEK 60 parts | IPA 20 parts | 5.58 parts | 1.50 | 211 | 1.37 | 0.20 | Δ |

It is recognized that from a result of tables 15 and 16, the span of the resin particle dispersion using the resin of the present invention is 0.8 to 1.2 and has a narrow particle size distribution. Further, it is recognized that the resin particle dispersion has a good storage stability, and even if the amount of ammonia water is small, it is possible to obtain a resin particle dispersion having an uniform particle size distribution.

(The Preparation of the Wax Particle Dispersion)

To 1000 parts of distilled water dissolved 25 parts of sodium dodecylbenzenesulfonate (NEOGEN SC; DAI-ICHI KOGYO SEIYAKU CO., LTD.) was added 268 parts of paraffin wax (HNP0190; Nippon Seiro Co., Ltd.) to emulsify and disperse and thereby obtaining a wax particle dispersion liquid.

(A Colorant Particle Dispersion)

To 1000 parts of distilled water dissolved 56 parts of sodium dodecylbenzenesulfonate (NEOGEN SC; DAI-ICHI KOGYO SEIYAKU CO., LTD.) was added 139 parts of carbon black (REGAL330R; Cabot Corporation) as a colorant particle to disperse and thereby obtaining a colorant particle dispersion.

Example 17

(A Manufacture of the Toner)

After 100 parts by weight of resin particle dispersion (1) (converted to solid content), 39 parts by weight of colorant dispersion, 23 parts by weight of wax particle dispersion were added to a vessel with a stirring) device, a condenser and a thermometer, and were controlled at 30° C. of an internal temperature, sodium hydroxide solution was added to adjust a pH to 11.0. Next, 240 parts of 1.2% by weight of magnesium chloride 6 hydrate solution was added with stirring. After added, a temperature was increased up to 90° C. and maintained for 3 hours. The produced particle was filtrated. After the obtained cake was washed repeatedly with an ion-exchange water until the rinse water shows a neutral, a toner particle (1) was obtained by drying with a hot-air dryer of 40° C. As to the toner particle (1), the volume average particle diameter was 5.8 μm, and the value of the volume average particle size distribution index, GSDv was 1.21.

Industrial Applicability

The unsaturated polyester resin using the compound of the present inventions make it possible to have an excellent performance on a water resistance, a shrinkage, a mechanical property as a binder resin for fiber-reinforced molded article comparing with the unsaturated polyester resin using a raw material derived from fossil fuel, and to produce the unsaturated polyester resin capable of decreasing environmental load, and containing a lot of raw material derived from biomass resources in the broad fields.

The polyester resin using the compound of the present inventions make it possible to produce the polyester resin capable of decreasing environmental load, and containing a lot of raw material derived from biomass resources in the broad fields.

The invention claimed is:

1. An unsaturated polyester resin wherein a compound is an essential component of an alcohol component;
    wherein the compound is represented by the following chemical formula [Chemical 1]:

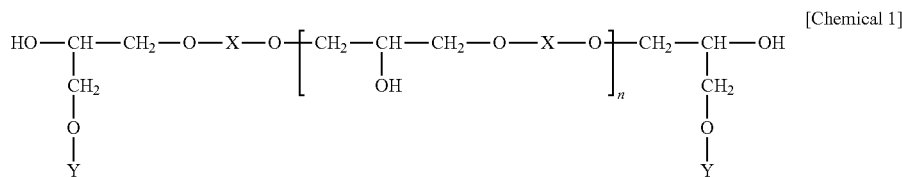

[Chemical 1]

wherein X is an aliphatic or an aromatic residue, Y is a refined rosin residue, a disproportionated rosin residue or a hydrogenated rosin residue, and n=0 to 1 in the formula.

2. An unsaturated polyester resin wherein a compound is an essential component of an alcohol component and is contained at 20 percent by weight or more as a raw material of an unsaturated polyester;
    wherein the compound is represented by the following chemical formula [Chemical 1]:

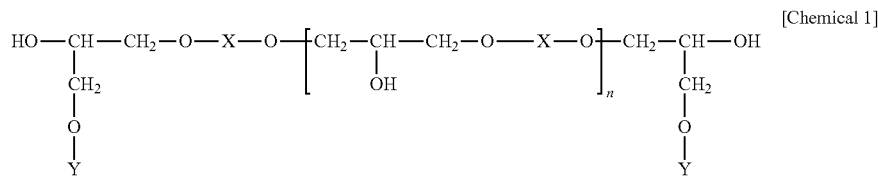

[Chemical 1]

wherein X is an aliphatic or an aromatic residue, Y is a refined rosin residue, a disproportionated rosin residue or a hydrogenated rosin residue, and n=0 to 1 in the formula.

3. A premix molding compound comprising the unsaturated polyester resin according to claim 1.

4. A premix molding compound according to claim 3, wherein the compound is a sheet molding compound, or a bulk molding compound.

5. A polyester resin wherein a compound shown in the following chemical formula [Chemical 1], is an essential component of an alcohol component:

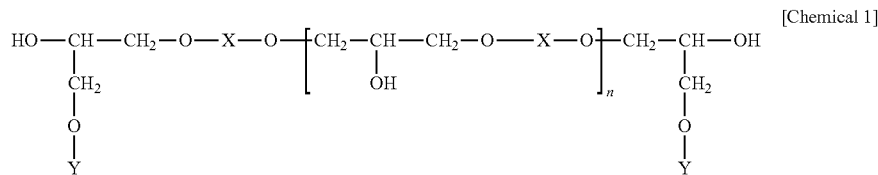

[Chemical 1]

wherein X is an aliphatic or an aromatic residue, Y is a refined rosin residue, a disproportionated rosin residue or a hydrogenated rosin residue, and n=0 to 1.

6. A polyester resin according to claim 5, wherein the compound is obtained by the addition reaction of one or more selected from the group consisting of a refined rosin, a disproportionated rosin, and a hydrogenated rosin, to an epoxy group of a compound having two epoxy groups in one molecule and shown in the following chemical formula [Chemical 2]:

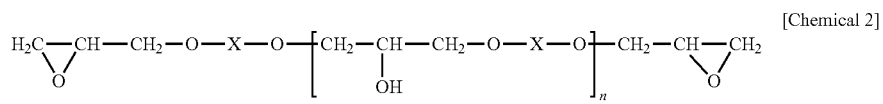

wherein X is an aliphatic or an aromatic residue, and n=0 to 1.

7. A polyester resin according to claim 5, wherein the compound according to claim 7 is contained at 20 percent by weight or more as a raw material of polyester.

8. A resin composition for a powder coating comprising the polyester resin according to claim 5.

9. A resin composition for an electrophotographic developer comprising the polyester resin according to claim 5.

10. An urethane acrylate resin comprising the polyester resin according to claim 5 that is modified by isocyanate.

11. A resin particle comprising a polyester resin wherein a compound shown in the following chemical formula[Chemical 1], is an essential component of an alcohol component of the polyester resin:

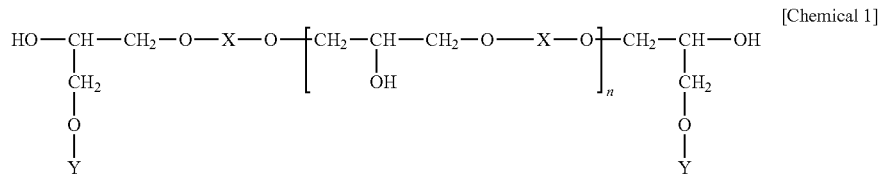

wherein X is an aliphatic or an aromatic residue, Y is a refined rosin residue, a disproportionated rosin residue or a hydrogenated rosin residue, and n=0 to 1.

12. A resin particle according to claim 11, wherein an average particle diameter of the resin particle is within a range from 0.01 to 1 μm.

13. A resin particle according to claim 11, wherein the resin particle is obtained by causing the phase inversion by means of adding a neutralizing agent and a water-based medium into a resin solution made by dissolving the polyester resin into an organic solvent, and thereby forming an O/W emulsion of resin particle, and further removing the organic solvent from a dispersion of an O/W emulsion of resin particle.

14. A resin particle according to claim 11, wherein the compound is obtained by the addition reaction of one or more selected from the group consisting of a refined rosin, a disproportionated rosin, and a hydrogenated rosin, to an epoxy group of a compound having two epoxy groups in one molecule and shown in the following chemical formula[Chemical 2]:

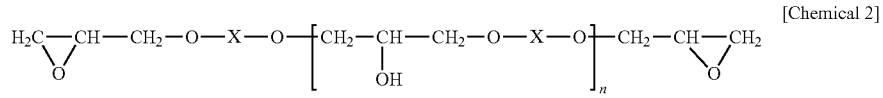

wherein X is an aliphatic or an aromatic residue, and n=0 to 1.

15. A resin particle according to claim 11, wherein the compound according to claim 13 is contained at 20 percent by weight or more as a raw material of polyester.

16. A resin particle according to claim 13, wherein the neutralizing agent is contained at 0.8 to 1.7 equivalent per equivalent of a carboxyl group contained in the polyester resin.

17. An electrophotographic toner, wherein the electrophotographic toner comprises at least a polyester resin and a colorant, and comprises a resin particle comprising the polyester resin wherein a compound shown in the following chemical formula [Chemical 1], is an essential component of an alcohol component of the polyester resin:

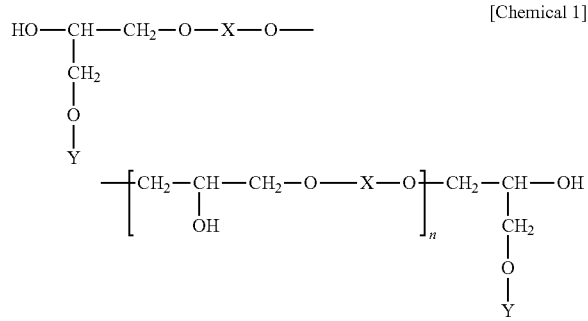

[Chemical 1]

wherein X is an aliphatic or an aromatic residue, Y is a refined rosin residue, a disproportionated rosin residue or a hydrogenated rosin residue, and n=0 to 1.

18. An electrophotographic toner according to claim 17, wherein an average particle diameter of the resin particle is within a range from 0.01 to 1 μm.

19. An electrophotographic toner according to claim 17, wherein the toner comprises a resin particle obtained by causing the phase inversion by means of adding a neutralizing agent and a water-based medium into a resin solution made by dissolving the polyester resin into an organic solvent, and thereby forming an O/W emulsion of resin particle, and further removing the organic solvent from a dispersion of an O/W emulsion of resin particle.

20. An electrophotographic toner according to claim 17, wherein the compound is obtained by the addition reaction of one or more selected from the group consisting of a refined rosin, a disproportionated rosin, and a hydrogenated rosin, to an epoxy group of a compound having two epoxy groups in one molecule and shown in the following chemical formula [Chemical 2]:

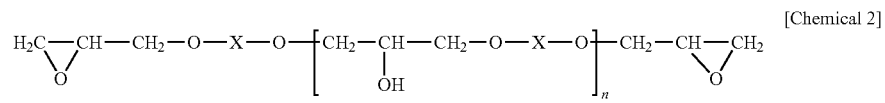

[Chemical 2]

wherein is an aliphatic or an aromatic residue, and n=0 to 1.

21. An electrophotographic toner according to claim 17, wherein the compound according to claim 19 is contained at 20 percent by weight or more as a raw material of polyester.

22. An electrophotographic toner according to claim 19, wherein the neutralizing agent is contained at 0.8 to 1.7 equivalent per equivalent of a carboxyl group contained in the polyester resin.

23. The unsaturated polyester resin according to claim 1, wherein the compound is obtained by the addition reaction of one or more rosins selected from the group consisting of a refined rosin, a disproportionated rosin, and a hydrogenated rosin, to an epoxy group of a compound having two epoxy groups in one molecule and shown in the following chemical formula [Chemical 2]:

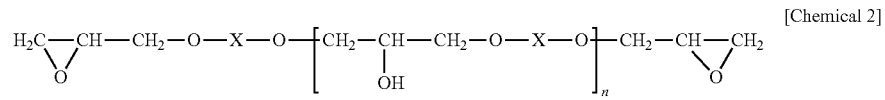

[Chemical 2]

wherein X is an aliphatic or an aromatic residue, and n=0 to 1.

24. The unsaturated polyester resin according to claim 2, wherein the compound is obtained by the addition reaction of one or more rosins selected from the group consisting of a refined rosin, a disproportionated rosin, and a hydrogenated rosin, to an epoxy group of a compound having two epoxy groups in one molecule and shown in the following chemical formula [Chemical 2]:

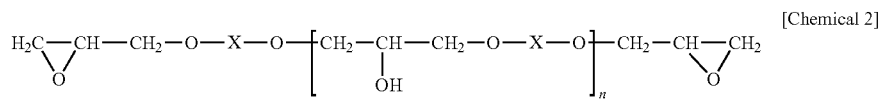

[Chemical 2]

wherein X is an aliphatic or an aromatic residue, and n=0 to 1.

* * * * *